United States Patent
Popovic

(10) Patent No.: US 11,344,379 B2
(45) Date of Patent: May 31, 2022

(54) AUTOMATIC MOTION CONTROL OF A DEPENDENT SURGICAL ROBOTIC ARM

(71) Applicant: KONINKLIJKE PHILIPS N.V., Eindhoven (NL)

(72) Inventor: Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 336 days.

(21) Appl. No.: 16/467,083

(22) PCT Filed: Dec. 6, 2017

(86) PCT No.: PCT/EP2017/081652
§ 371 (c)(1),
(2) Date: Jun. 6, 2019

(87) PCT Pub. No.: WO2018/104376
PCT Pub. Date: Jun. 14, 2018

(65) Prior Publication Data
US 2019/0307519 A1 Oct. 10, 2019

Related U.S. Application Data

(60) Provisional application No. 62/430,997, filed on Dec. 7, 2016.

(51) Int. Cl.
*A61B 34/32* (2016.01)
*A61B 34/30* (2016.01)
(Continued)

(52) U.S. Cl.
CPC .............. *A61B 34/32* (2016.02); *A61B 34/30* (2016.02); *A61B 90/361* (2016.02);
(Continued)

(58) Field of Classification Search
CPC ....... A61B 34/32; A61B 34/30; A61B 90/361; A61B 2034/302; A61B 2090/364;
(Continued)

(56) References Cited

U.S. PATENT DOCUMENTS 8,551,114 B2 10/2013 De La Pena
2010/0331858 A1 12/2010 Simaan
(Continued)

FOREIGN PATENT DOCUMENTS

WO 2015/121765 8/2015

OTHER PUBLICATIONS

International Search Report and Written Opinion dated Mar. 20, 2018 for International Application No. PCT/EP2017/081652 filed Dec. 6, 2017.

*Primary Examiner* — Basil T. Jos

(57) ABSTRACT

A motion dependency surgical robotic system (100) employs an independent robotic arm (20) including a first surgical instrument, a dependent robotic arm (21) including a second surgical instrument, and a motion dependency robot controller (104). In operation, the motion dependency robot controller (104) controls an independent motion of the independent robotic arm (20) within a coordinate space responsive to an input signal indicative of the motion of the independent robotic arm (20) within the coordinate space, and further controls a motion of the dependent robotic arm (21) within the coordinate space as a function of a spatial geometric relationship between the independent robotic arm (20) and the dependent robotic arm (21) within the coordinate space. The spatial geometric relationship defines a procedural synchronization between the independent robotic arm (20) and the dependent robotic arm (21) in a synchronized execution of a surgical task by the surgical instruments.

21 Claims, 17 Drawing Sheets

(51) Int. Cl.
*A61B 90/00* (2016.01)
*B25J 9/16* (2006.01)

(52) U.S. Cl.
CPC ........... *B25J 9/1682* (2013.01); *B25J 9/1689* (2013.01); *A61B 2034/302* (2016.02); *A61B 2090/364* (2016.02); *G05B 2219/39212* (2013.01); *G05B 2219/39389* (2013.01)

(58) Field of Classification Search
CPC ................. B25J 9/1682; B25J 9/1689; G05B 2219/39212; G05B 2219/39389
See application file for complete search history.

(56) References Cited

U.S. PATENT DOCUMENTS

| | | |
|---|---|---|
| 2012/0265071 A1 | 10/2012 | Berke |
| 2013/0325030 A1 | 12/2013 | Hourtash |
| 2013/0331644 A1 | 12/2013 | Pandya |
| 2014/0094968 A1 | 4/2014 | Taylor |
| 2015/0297177 A1 | 10/2015 | Boctor |
| 2016/0184032 A1* | 6/2016 | Romo .................... A61B 10/04 606/130 |

* cited by examiner

INDEPENDENT ROBOTIC ARM
20

$MV_{IRA} = f(IS_{IRA})$

LOCATION POSITIONING: $[X\ Y\ Z]_{IRA}$
ORIENTATION POSITIONING: $[X\ Y\ Z\ \Phi\ \Theta\ \Psi]_{IRA}$
TRANSLATIONAL VELOCITY: $[dX/dt\ dY/dt\ dZ/dt]_{IRA}$
ANGULAR VELOCITY: $[dX/dt\ dY/dt\ dZ/dt\ d\Phi/dt\ d\Theta/dt\ d\Psi/dt]_{IRA}$

DEPENDENT ROBOTIC ARM
21

$MV_{DRA} = f(SGR, MV_{IRA})$

LOCATION POSITIONING: $[X\ Y\ Z]_{DRA}$
ORIENTATION POSITIONING: $[X\ Y\ Z\ \Phi\ \Theta\ \Psi]_{DRA}$
TRANSLATIONAL VELOCITY: $[dX/dt\ dY/dt\ dZ/dt]_{DRA}$
ANGULAR VELOCITY: $[dX/dt\ dY/dt\ dZ/dt\ d\Phi/dt\ d\Theta/dt\ d\Psi/dt]_{DRA}$

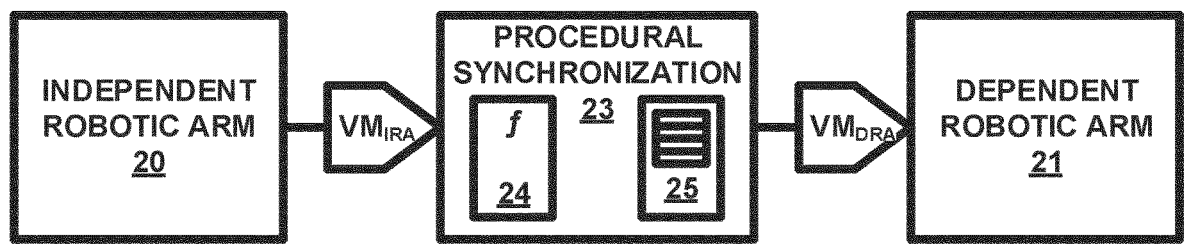
FIG. 6A
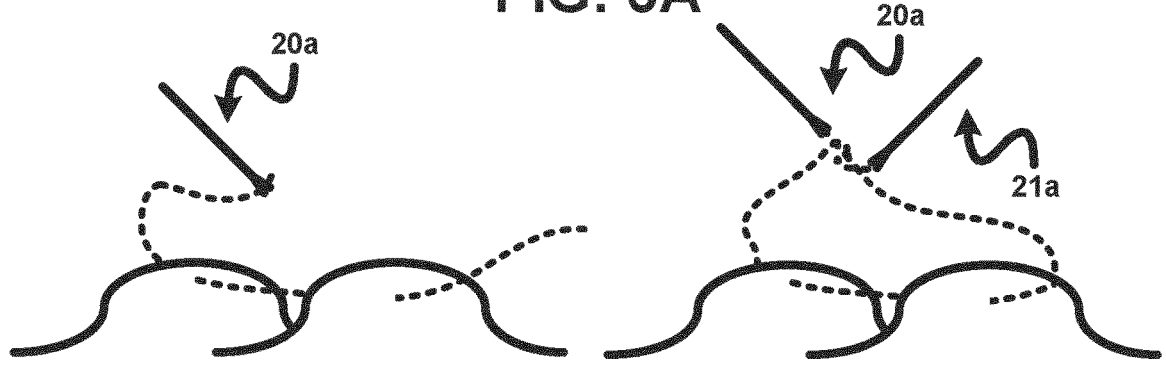
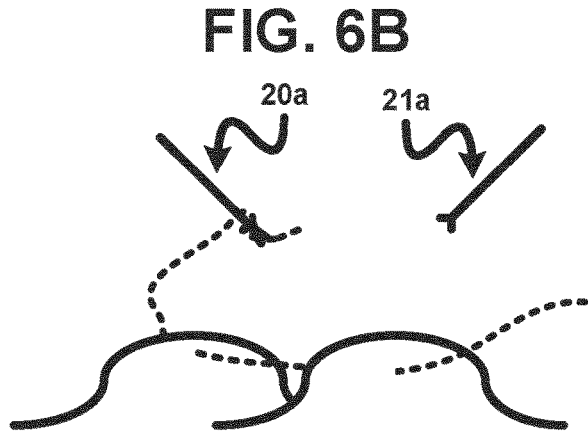
FIG. 6B
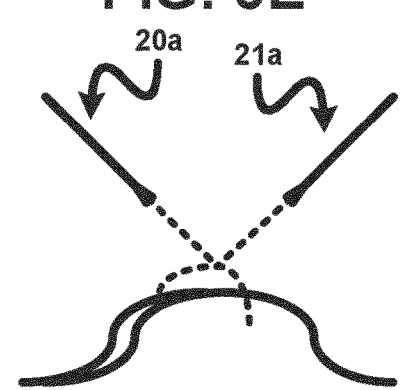
FIG. 6E
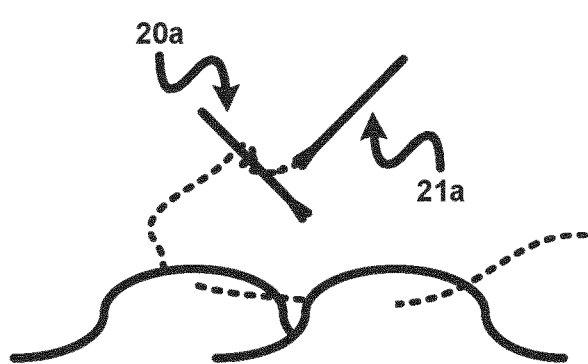
FIG. 6C
FIG. 6F
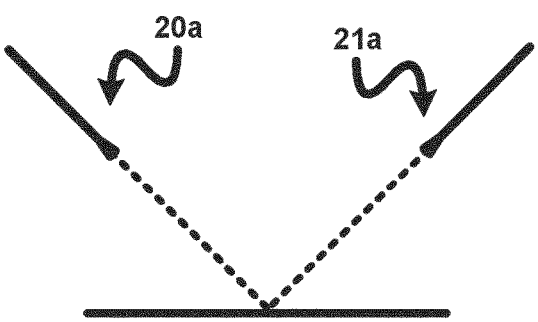
FIG. 6D
FIG. 6G

INDEPENDENT ROBOTIC ARM
20

$MV_{IRA1} = f(IS_{IRA1})$

LOCATION POSITIONING: $[X\ Y\ Z]_{IRA1}$
ORIENTATION POSITIONING: $[X\ Y\ Z\ \Phi\ \Theta\ \Psi]_{IRA1}$
TRANSLATIONAL VELOCITY: $[dX/dt\ dY/dt\ dZ/dt]_{IRA1}$
ANGULAR VELOCITY: $[dX/dt\ dY/dt\ dZ/dt\ d\Phi/dt\ d\Theta/dt\ d\Psi/dt]_{IRA1}$

INDEPENDENT ROBOTIC ARM
22

$MV_{IRA2} = f(IS_{IRA2})$

LOCATION POSITIONING: $[X\ Y\ Z]_{IRA2}$
ORIENTATION POSITIONING: $[X\ Y\ Z\ \Phi\ \Theta\ \Psi]_{IRA2}$
TRANSLATIONAL VELOCITY: $[dX/dt\ dY/dt\ dZ/dt]_{IRA2}$
ANGULAR VELOCITY: $[dX/dt\ dY/dt\ dZ/dt\ d\Phi/dt\ d\Theta/dt\ d\Psi/dt]_{IRA2}$

DEPENDENT ROBOTIC ARM
21

$MV_{DRA1} = f(SGR, MV_{IRA1}, MV_{IRA1})$

LOCATION POSITIONING: $[X\ Y\ Z]_{DRA}$
ORIENTATION POSITIONING: $[X\ Y\ Z\ \Phi\ \Theta\ \Psi]_{DRA}$
TRANSLATIONAL VELOCITY: $[dX/dt\ dY/dt\ dZ/dt]_{DRA}$
ANGULAR VELOCITY: $[dX/dt\ dY/dt\ dZ/dt\ d\Phi/dt\ d\Theta/dt\ d\Psi/dt]_{DRA}$

AUTOMATIC MOTION CONTROL OF A DEPENDENT SURGICAL ROBOTIC ARM

CROSS REFERENCE TO RELATED APPLICATIONS

This application is the U.S. National Phase application under 35 U.S.C. § 371 of International Application No. PCT/EP2017/081652 filed Dec. 6, 2017, published as WO 2018/104376 on Jun. 14, 2018, which claims the benefit of U.S. Provisional Patent Application No. 62/430,997 on Dec. 7, 2016. These applications are hereby incorporated by reference herein.

FIELD OF THE INVENTION

The inventions of the present disclosure generally relate to surgical robotic systems employing two or more surgical robotic arms (e.g., the da Vinci® Surgical System, the Raven Robotic Surgical System, the Sport™ Surgical System, the Flex™ Robotic System, etc.). The inventions of the present disclosure more particularly relate to improving such surgical robotic systems by providing an automatic motion control of one surgical robotic arm dependent upon an independent operator control of another surgical robotic arm.

BACKGROUND OF THE INVENTION

Currently, surgical robotic arms of a surgical robotic system are controlled from a surgeon console. Generally, an operator moves handles on the console whereby signals from the handles are interpreted and translated into the motion of the surgical robotic arms. More particularly, each surgical robotic arm is operated independently of the other surgical robotic arm(s), which requires the operator to frequently switch control between the surgical robotic arms. This frequent control switching between surgical robotic arms may cause workflow issues.

In addition, in many multi-robotic arm surgical tasks, the motion of one surgical robotic arm may be dependent upon the motion of another surgical robotic arm for purposes of executing the surgical task. For example, in laparoscopic surgery, the maneuver of knot tying is a synchronized effort of two surgical robotic arms. In another example, pick and place surgical tasks (e.g. suture sponge or imaging device) also require a synchronized motion of surgical robotic arms. By further example, some surgical tasks (e.g. cut and cauterize) designate one surgical robotic arm to be a leading surgical robotic arm and another surgical robotic arm as a follower surgical robotic arm (e.g., the follower surgical robotic arm follows the leading surgical robotic arm at a fixed distance along a line). Additionally, for example, if a surgical robotic arm is holding an endoscope and two additional surgical robotic arms are respectively holding instruments, then a motion of the robotically held endoscope depends on position of the robotically held instruments with the goal of keeping the instruments in view of the endoscope.

Clearly, a success or a failure of multi-robotic arm surgical tasks heavily depend upon the skills of the surgeon console operator to frequently switch the control between surgical robotic arms.

SUMMARY OF THE INVENTION

To improve upon dependent motion among surgical robotic arms involved in multi-robotic arm surgical tasks, the present disclosure provides inventions for controlling two or more surgical robotic arms using one or more input devices (e.g., handle(s), joystick(s), roller ball(s), etc.) by interpreting and translating signals from the input device(s) into motion of an independent surgical robotic arm whereby any motion of one or more dependent surgical robotic arms is defined by a spatial geometric relationship to the motion of the independent surgical robotic arm. The improvement by the inventions of the present disclosure is an intuitive control of multi-robotic arm surgical tasks with a reduced need to switch control between the surgical robotic arms.

For purposes of describing and claiming the inventions of the present disclosure:

(1) the term "spatial geometric relationship" broadly encompasses a motion dependency between multiple surgical robotic arms within a coordinate space defined by a motion vector in the form of a linear vector and/or an angular vector, and may be further defined by a magnitude and/or a direction of the motion vector relative to an axis or a plane within the coordinate space or relative to a geometric object within the coordinate space;

(2) the term "independent surgical robotic arm" broadly encompasses all structural configuration of a surgical robotic arm, as known in the art of the present disclosure and hereinafter conceived, having a range of motion within a coordinate space controlled by an input device as known in the art of the present disclosure; and (3) the term "dependent surgical robotic arm" broadly encompasses all structural configuration of a surgical robotic arm, as known in the art of the present disclosure and hereinafter conceived, having a range of motion within a coordinate space automatically controlled in accordance with the inventive principles of the present disclosure.

One example of a spatial geometric relationship in accordance with the inventive principles of the present disclosure between an independent surgical robotic arm and a dependent surgical robotic arm is a defined linear vector between the surgical robotic arms within the coordinate space. An automatic motion control of the dependent surgical robotic arm maintains a distance between the surgical robotic arms equal to the magnitude of the linear vector with a direction of the linear vector varying as the dependent surgical robotic arm follows a path of the independent surgical robotic arm within the coordinate space as controlled by an operator of the input device(s) (e.g., handle(s), joystick(s), roller ball(s), etc.).

A second example of a spatial geometric relationship in accordance with the inventive principles of the present disclosure between an independent surgical robotic arm and a dependent surgical robotic arm is a defined linear vector between the surgical robotic arms within the coordinate space with the linear vector having a direction parallel to an axis of the coordinate space, a direction traversing a plane of the coordinate space, or a direction radial to a surface of a sphere. As an operator of the input device(s) exercises motion control of the independent surgical robotic arm within the coordinate space, an automatic motion control of the dependent surgical robotic arm maintains a distance between the surgical robotic arms equal to the magnitude of the linear vector and further maintains a direction of the dependent surgical robotic arm corresponding to a direction of the vector parallel to the axis, traversal to the plane or radial to the sphere.

A third example of a spatial geometric relationship in accordance with the inventive principles of the present disclosure between an independent surgical robotic arm and a dependent surgical robotic arm is a defined angular vector between the surgical robotic arms within the coordinate space. An automatic motion control of the dependent surgical robotic arm maintains an angular orientation between the surgical robotic arms equal to the magnitude of the angular vector with a direction of the angular vector varying as the dependent surgical robotic arm trails a path of the independent surgical robotic arm within the coordinate space as controlled by an operator of the input device(s) (e.g., handle(s), joystick(s), roller ball(s), etc.).

A fourth example of a spatial geometric relationship in accordance with the inventive principles of the present disclosure between an independent surgical robotic arm and a dependent surgical robotic arm is a defined angular vector between the surgical robotic arms within the coordinate space with the angular vector having a direction traversing a plane of the coordinate space. As an operator of the input device(s) exercises motion control of the independent surgical robotic arm within the coordinate space, an automatic motion control of the dependent surgical robotic arm maintains an angular orientation between the surgical robotic arms equal to the magnitude of the angular vector and further maintains a direction of the dependent surgical robotic arm corresponding to a direction of the angular vector traversal to the plane.

A fifth example of a spatial geometric relationship in accordance with the inventive principles of the present disclosure between an independent surgical robotic arm and a dependent surgical robotic arm is a defined procedural synchronization between the surgical robotic arms in an execution of a surgical task (e.g., knot tying in a laparoscopic surgery). An automatic motion control of the dependent surgical robotic arm within the coordinate space is a function of a motion of the independent surgical robotic arm within the coordinate space as an operator of the input device(s) exercises motion control of the independent surgical robotic arm within the coordinate space in accordance with a particular surgical procedure (e.g., automatic motion control of the dependent surgical robotic arm is computed via an explicit function defined by the procedural synchronization or retrieved via a lookup table defining the procedural synchronization).

A sixth example of a spatial geometric relationship in accordance with the inventive principles of the present disclosure between a pair of independent surgical robotic arms and a dependent surgical robotic arm is a defined relative positioning between the surgical robotic arms within the coordinate space. An automatic motion control of the dependent surgical robotic arm maintains the relative positioning between the surgical robotic arms as an operator of the input device exercises motion control of the independent surgical robotic arms within the coordinate space.

Additionally, a spatial geometric relationship of the present disclosure may be implemented during specified time period(s) or an entirety of a robotic surgical procedure, may be implemented for specific task(s) or all tasks of a robotic surgical procedure, may have a conditional definition or a fixed definition, and may be defined as a function of time.

Also for purposes of describing and claiming the inventions of the present disclosure:

(1) the term "motion dependency surgical robotic system" broadly encompasses all surgical robotic systems, as known in the art of the present disclosure and hereinafter conceived, incorporating the inventive principles of the present disclosure for controlling two or more surgical robotic arms by processing input signals from input device(s) into motion of an independent surgical robotic arm whereby any motion of one or more dependent surgical robotic arms is defined by a spatial geometric relationship of the dependent surgical robotic arm to the independent surgical robotic arm. Examples of known surgical robotic systems include, but are not limited to, the da Vinci® Surgical System, the Raven Robotic Surgical System, the Sport™ Surgical System and the Flex™ Robotic System;

(2) the term "motion dependency robot control method" broadly encompasses all methods of controlling a surgical robotic system, as known in the art of the present disclosure and hereinafter conceived, incorporating the inventive principles of the present disclosure for controlling two or more surgical robotic arms by processing input signals from input device(s) into motion of an independent surgical robotic arm whereby any motion of one or more dependent surgical robotic arms is defined by a spatial geometric relationship of the dependent surgical robotic arm to the independent surgical robotic arm;

(3) the term "motion dependency robot controller" broadly encompasses all structural configurations of an application specific main board or an application specific integrated circuit housed employed within a motion dependency surgical robotic system of the present disclosure for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), interface(s), bus(es), slot(s) and port(s);

(4) the term "application module" broadly encompasses a component of the motion dependency robot controller consisting of an electronic circuit and/or an executable program (e.g., executable software and/or firmware stored on non-transitory computer readable medium(s)) for executing a specific application; and (5) the terms "signal", "data" and "command" broadly encompasses all forms of a detectable physical quantity or impulse (e.g., voltage, current, or magnetic field strength) as understood in the art of the present disclosure and as exemplary described herein for communicating information and/or instructions in support of applying various inventive principles of the present disclosure as subsequently described herein. Signal/data/command communication between components of the present disclosure may involve any communication method, as known in the art of the present disclosure and hereinafter conceived, including, but not limited to, data/command transmission/reception over any type of wired or wireless medium/datalink and a reading of signal/data/commands uploaded to a computer-usable/computer readable storage medium.

One embodiment of the inventions of the present disclosure is a motion dependency surgical robotic system employing an independent surgical robotic arm, a dependent surgical robotic arm, and a motion dependency robot controller in communication with the independent surgical robotic arm and the dependent surgical robotic arm.

In operation, the motion dependency robot controller controls a motion of the independent surgical robotic arm within a coordinate space responsive to an input signal indicative of the motion of the independent surgical robotic arm within the coordinate space. The motion dependency robot further controls a motion of the dependent surgical robotic arm within the coordinate space as a function of a spatial geometric relationship between the independent surgical robotic arm and the dependent surgical robotic arm within the coordinate space.

A second embodiment of the inventions of the present disclosure is the motion dependency robot controller application modules employing an independent motion vector generator, an independent surgical robotic arm actuator, a dependent motion vector generator, and a dependent surgical robotic arm actuator.

In operation, the independent motion vector generator generates an independent motion vector signal (e.g., a linear vector or an angular vector) for controlling a motion of an independent surgical robotic arm within a coordinate space responsive to an input signal indicative of the motion of the independent surgical robotic arm within the coordinate space.

The independent surgical robotic arm actuator generates independent actuation commands instructive of the motion of the independent surgical robotic arm within the coordinate space responsive to a generation of the independent motion vector signal by the independent motion vector generator.

The dependent motion vector generator generates a dependent motion vector signal (e.g., a linear vector or an angular vector) for controlling a motion of the dependent surgical robotic arm within the coordinate space as a function of a spatial geometric relationship between the independent surgical robotic arm and the dependent surgical robotic arm within the coordinate space.

The dependent surgical robotic arm actuator generates actuation commands instructive of the motion of the dependent surgical robotic arm within the coordinate space responsive to a generation of the dependent motion vector signal by the dependent motion vector generator.

A third form embodiment of the inventions of the present disclosure is a motion dependency robot control method of the motion dependency surgical robotic system.

The motion dependency robot control method involves the motion dependency robot controller controlling the motion of the independent surgical robotic arm within the coordinate space responsive to the input signal indicative of the motion of the independent surgical robotic arm within the coordinate space, and the motion dependency robot controller controlling the motion of the dependent surgical robotic arm within the coordinate space as a function of the spatial geometric relationship between the independent surgical robotic arm and the dependent surgical robotic arm within the coordinate space.

The foregoing embodiments and other embodiments of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

BRIEF DESCRIPTION OF THE DRAWINGS

FIG. 1 illustrates exemplary embodiments of spatial geometric relationships between an independent surgical robotic arm and a dependent surgical robotic arm in accordance with the inventive principles of the present disclosure.

FIGS. 6A-6G illustrate an exemplary embodiment of a procedural synchronization between an independent surgical robotic arm and a dependent surgical robotic arm in accordance with the inventive principles of the present disclosure.

FIG. 10 illustrates exemplary embodiments of a spatial geometric relationship between a pair of independent surgical robotic arms and a dependent surgical robotic arm in accordance with the inventive principles of the present disclosure.

DETAILED DESCRIPTION OF THE PREFERRED EMBODIMENTS

Figure 2A:
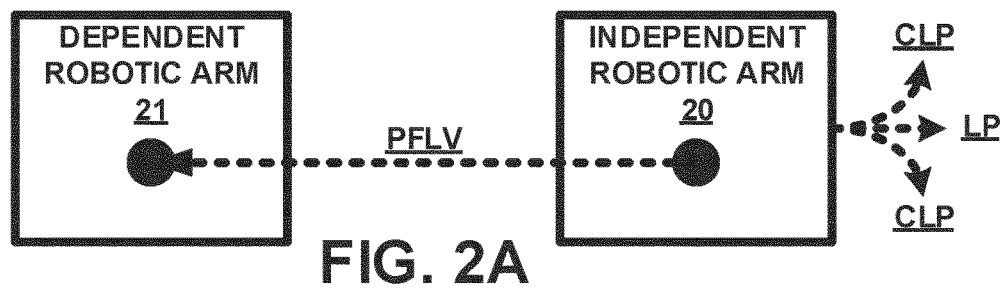
FIGS. 2A-2E illustrate exemplary embodiments of a spatial distance between an independent surgical robotic arm and a dependent surgical robotic arm in accordance with the inventive principles of the present disclosure.

To facilitate an understanding of the inventions of the present disclosure, the following description of FIGS. 1-5 teaches basic inventive principles of a spatial geometric relationship between an independent surgical robotic arm and a dependent surgical robotic arm in accordance with the inventive principles of the present disclosure. From this description of FIGS. 1-5, those having ordinary skill in the art will appreciate how to apply the inventive principles of the present disclosure to practice numerous and various spatial geometric relationships between an independent surgical robotic arm and a dependent surgical robotic arm.

Referring to FIG. 1, a three-dimensional ("3D") coordinate space CS, symbolized by the X-Y axes as shown for clarity, represents an operating space for performing a surgical robotic procedure (e.g., general surgical procedures, cardiac surgical procedures, neurosurgery, etc.). In practice, coordinate space CS may be established by a support of an anatomical region of a patient within the operating space (e.g., a patient table).

A motion vector $MV_{IRA}$ of an independent surgical robotic arm 20 within coordinate space CS is controllable as known in the art of the present disclosure by an input device of a surgical robot system (not shown) (e.g., handle(s), joystick(s), roller ball(s), etc.). More particularly, the motion vector $MV_{IRA}$ of an independent surgical robotic arm 20 within coordinate space CS is a function of an input signal $IS_{IRA}$ generated by the input device directing a translation, a rotation and/or a pivoting of independent surgical robotic arm 20 within coordinate space CS.

A translation, a rotation and/or a pivoting of a dependent surgical robotic arm 21 within coordinate space CS is automatically controlled by a spatial geometrical relationship SGR of the present disclosure between independent surgical robotic arm 20 and dependent surgical robotic arm 21. More particularly, a motion vector $MV_{DRA}$ of dependent surgical robotic arm 21 within coordinate space CS is a function of motion vector $MV_{IRA}$ of an independent surgical robotic arm 20 within coordinate space CS in the context of spatial geometrical relationship SGR to thereby automatically control a translation, a rotation and/or a pivoting of dependent surgical robotic arm 21 within coordinate space CS.

In practice, the motion vector $MV_{IRA}$ of independent surgical robotic arm 20 and the motion vector $MV_{DRA}$ of dependent surgical robotic arm 21 may be derived as targeted positions of surgical robotic arms 20 and 21 within coordinate system CS.

In one embodiment, the motion vector $MV_{IRA}$ of an independent surgical robotic arm 20 and the motion vector $MV_{DRA}$ of an dependent surgical robotic arm 21 may be derived from three (3) targeted positions of surgical robotic arms 20 and 21 within coordinate system CS in accordance with $[X\ Y\ Z]_{IRA}$ and $[X\ Y\ Z]_{DRA}$.

In a second embodiment, the motion vector $MV_{IRA}$ of an independent surgical robotic arm 20 and the motion vector $MV_{DRA}$ of an dependent surgical robotic arm 21 may be derived from three (3) targeted positions and three (orientations) of surgical robotic arms 20 and 21 within coordinate system CS in accordance with $[X\ Y\ Z\ \Phi\ \Theta\ \psi]_{IRA}$ and $[X\ Y\ Z\ \Phi\ \Theta\ \psi]_{DRA}$.

Also in practice, the motion vector $MV_{IRA}$ of independent surgical robotic arm 20 and the motion vector $MV_{DRA}$ of dependent surgical robotic arm 21 may be derived as targeted velocities of a current orientation of surgical robotic arms 20 and 21 within coordinate system CS.

In one embodiment, the motion vector $MV_{IRA}$ of an independent surgical robotic arm 20 and the motion vector $MV_{DRA}$ of an dependent surgical robotic arm 21 may be derived as three (3) translational velocities of surgical robotic arms 20 and 21 within coordinate space CS in accordance with $[dX/dt\ dY/dt\ dZ/dt]_{IRA}$ and $[dX/dt\ dY/dt\ dZ/dt]_{DRA}$.

In a second embodiment, the motion vector $MV_{IRA}$ of an independent surgical robotic arm 20 and the motion vector $MV_{DRA}$ of an dependent surgical robotic arm 21 may be derived three (3) translational velocities and three (3) angular velocities of surgical robotic arms 20 and 21 within coordinate space CS in accordance with $[dX/dt\ dY/dt\ dZ/dt\ d\Phi/dt\ d\Theta/dt\ d\psi/dt]_{IRA}$ and $[dX/dt\ dY/dt\ dZ/dt\ d\Phi/dt\ d\Theta/dt\ d\psi/dt]_{DRA}$.

The spatial geometric relationship SGR is a motion dependency of dependent surgical robotic arm 21 on an operator controlled motion of independent surgical robotic arm 20 within coordinate space CS. More particularly, the spatial geometric relationship SGR defines a motion vector in the form of a linear vector and/or an angular vector, and may be further defined by a magnitude and/or a direction of the motion vector relative to an axis or a plane within the coordinate space or relative to a geometric object within the coordinate space.

The following description of FIGS. 2-5 illustrates various examples of a spatial geometric relationship SGR between surgical robotic arms 20 and 21.

Referring to FIG. 2A, a path following linear vector PFLV between surgical robotic arms 20 and 21 defines a spatial geometric relationship SGR whereby an automatic motion control of dependent surgical robotic arm 21 maintains a spatial distance between the surgical robotic arms 20 and 21 equal to a magnitude of path following linear vector PFLV with a direction of path following linear vector PFLV varying as dependent surgical robotic arm 21 follows a linear path LP and/or a curvilinear path CLP of independent surgical robotic arm 20 within the coordinate space CS (FIG. 1) as controlled by an operator of input device(s) (e.g., handle(s), joystick(s), roller ball(s), etc.).

In practice, while the direction of path following linear vector PFLV is variable in dependence of the motion of independent surgical robotic arm 20 within coordinate system CS, the magnitude of path following linear vector PFLV may be fixed or variable under specific condition(s). For example, the magnitude of path following linear vector PFLV may be reduced as surgical robotic arms 20 and 21 approach a targeted position within coordinate space CS or may attenuate over time as surgical robotic arms 20 and 21 are translated, rotated and/or pivoted within coordinate space CS.

Also in practice, for an implementation of path following linear vector PFLV, an orientation of dependent surgical robotic arm 21 within coordinate space CS may be dependent or independent of an orientation of independent surgical robotic arm 20 within coordinate space CS.

Figure 2B:
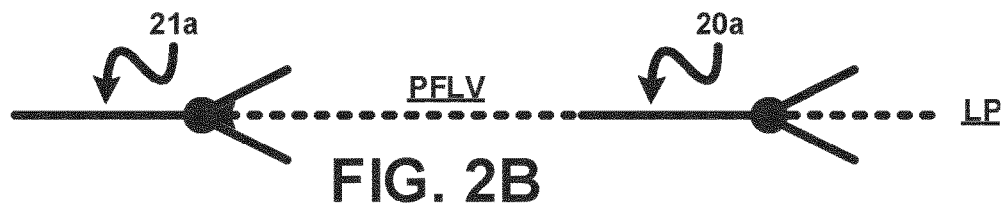

For example, FIG. 2B illustrates an automatic motion control of a dependent surgical robotic arm 21a maintaining a spatial distance, fixed or variable, between the surgical robotic arms 20a and 21a equal to the magnitude of path following linear vector PFLV as dependent surgical robotic arm 21a follows a linear path LP of independent surgical robotic arm 20a within the coordinate space CS. For this example, automatic motion control of dependent surgical robotic arm 21a involves an orientation of dependent surgical robotic arm 21a within coordinate space CS that is dependent upon an orientation of independent surgical robotic arm 20a within coordinate space CS (e.g., robotic arms 20a and 21a maintain identical orientations within coordinate space CS or a fixed relative orientations within coordinate space CS).

Figure 2C:
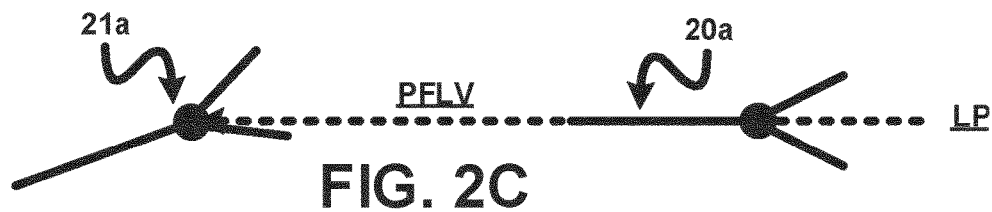

By further example, FIG. 2C illustrates an automatic motion control of dependent surgical robotic arm 21a maintaining a spatial distance, fixed or variable, between the surgical robotic arms 20a and 21a equal to the magnitude of path following linear vector PFLV as dependent surgical robotic arm 21a follows a linear path LP of independent surgical robotic arm 20a within the coordinate space CS. For this example, automatic motion control of dependent surgical robotic arm 21a involves an orientation of dependent surgical robotic arm 21a within coordinate space CS that is independent upon an orientation of independent surgical robotic arm 20a within coordinate space CS (e.g., robotic arms 20a and 21a have variable relative orientations within coordinate space CS).

Figure 2D:
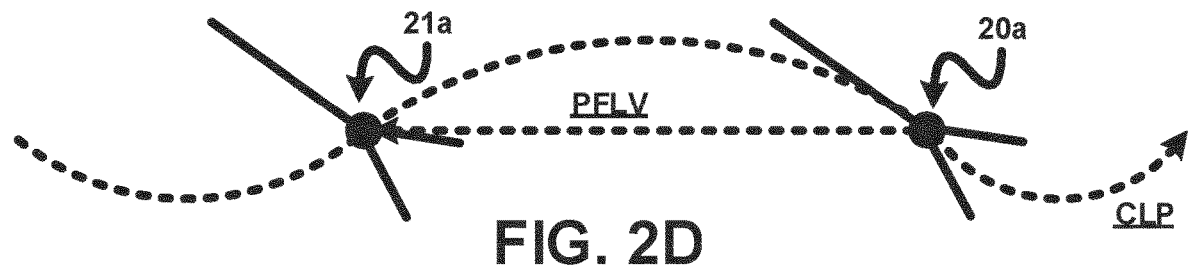

By further example, FIG. 2D illustrates an automatic motion control of a dependent surgical robotic arm 21a maintaining a spatial distance, fixed or variable, between the surgical robotic arms 20a and 21a equal to the magnitude of path following linear vector PFLV as dependent surgical robotic arm 21a follows a curvilinear path CLP of independent surgical robotic arm 20a within the coordinate space CS. For this example, automatic motion control of dependent surgical robotic arm 21a involves an orientation of dependent surgical robotic arm 21a within coordinate space CS that is dependent upon an orientation of independent surgical robotic arm 20a within coordinate space CS.

Figure 2E:
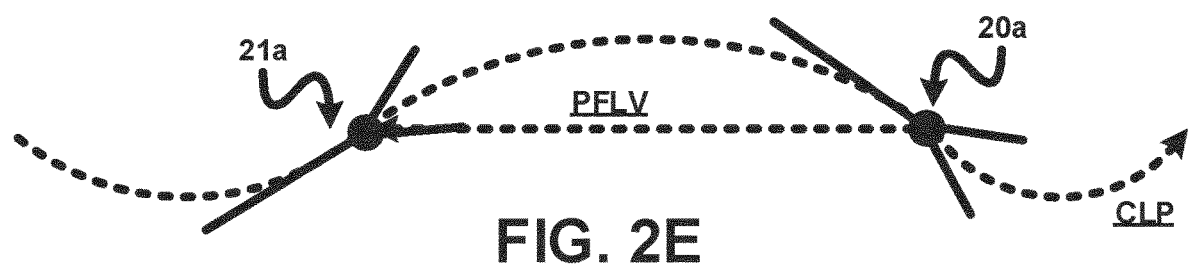

By further example, FIG. 2E illustrates an automatic motion control of dependent surgical robotic arm 21a maintaining a spatial distance, fixed or variable, between the surgical robotic arms 20a and 21a equal to the magnitude of path following linear vector PFLV as dependent surgical robotic arm 21a follows a curvilinear path CLP of independent surgical robotic arm 20a within the coordinate space CS. For this example, automatic motion control of dependent surgical robotic arm 21a involves an orientation of dependent surgical robotic arm 21a within coordinate space CS that is independent upon an orientation of independent surgical robotic arm 20a within coordinate space CS.

Figure 3A:
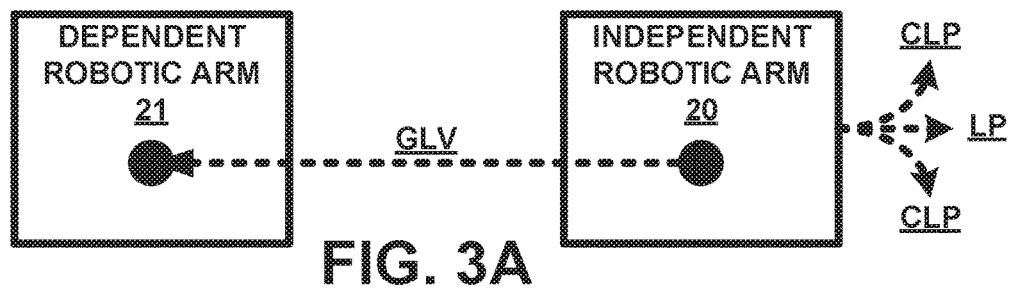
FIGS. 3A-3D illustrate additional exemplary embodiment of a spatial distance between an independent surgical robotic arm and a dependent surgical robotic arm in accordance with the inventive principles of the present disclosure.

Referring to FIG. 3A, a geometric linear vector GLV between surgical robotic arms 20 and 21 defines a spatial geometric relationship SGR whereby, as an operator of the input device(s) exercises motion control of the independent surgical robotic arm 20 within the coordinate space CS, an automatic motion control of dependent surgical robotic arm 21 maintains a spatial distance between surgical robotic arms 20 and 21 equal to a magnitude of geometric linear vector GLV and further maintains a direction of dependent surgical robotic arm 21 corresponding to a direction of the geometric liner vector GLV parallel to an axis of coordinate space CS, traversal of a plane of coordinate space CS or a radial to a surface of a sphere.

In practice, while the direction of geometric linear vector GLV is variable in dependence upon the motion of independent surgical robotic arm 20 within coordinate system CS, the magnitude of geometric linear vector GLV may be fixed or variable under specific condition(s). For example, the magnitude of geometric linear vector GLF may be reduced as surgical robotic arms 20 and 21 approach a targeted position within coordinate space CS or may attenuate over time as surgical robotic arms 20 and 21 are translated, rotated and/or pivoted within coordinate space CS.

Also in practice, for an implementation of geometric linear vector GLV, an orientation of dependent surgical robotic arm 21 within coordinate space CS may be dependent upon or independent of an orientation of independent surgical robotic arm 20 within coordinate space CS.

Figure 3B:
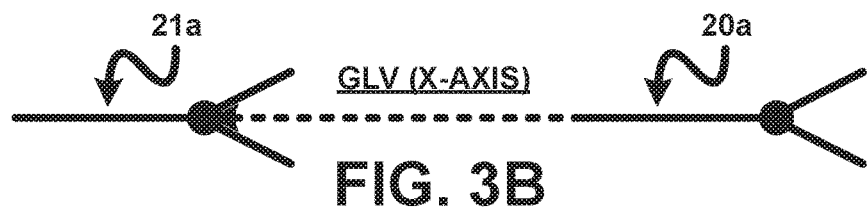

For example, FIG. 3B illustrates an automatic motion control of a dependent surgical robotic arm 21a maintaining a spatial distance, fixed or variable, between the surgical robotic arms 20a and 21a equal to the magnitude of geometric linear vector GLV with the direction of geometric linear vector V being parallelly fixed to the X-axis of coordinate space CS. For this example, automatic motion control of dependent surgical robotic arm 21a involves an orientation of dependent surgical robotic arm 21a within coordinate space CS that is dependent upon an orientation of independent surgical robotic arm 20a within coordinate space CS.

Figure 3C:
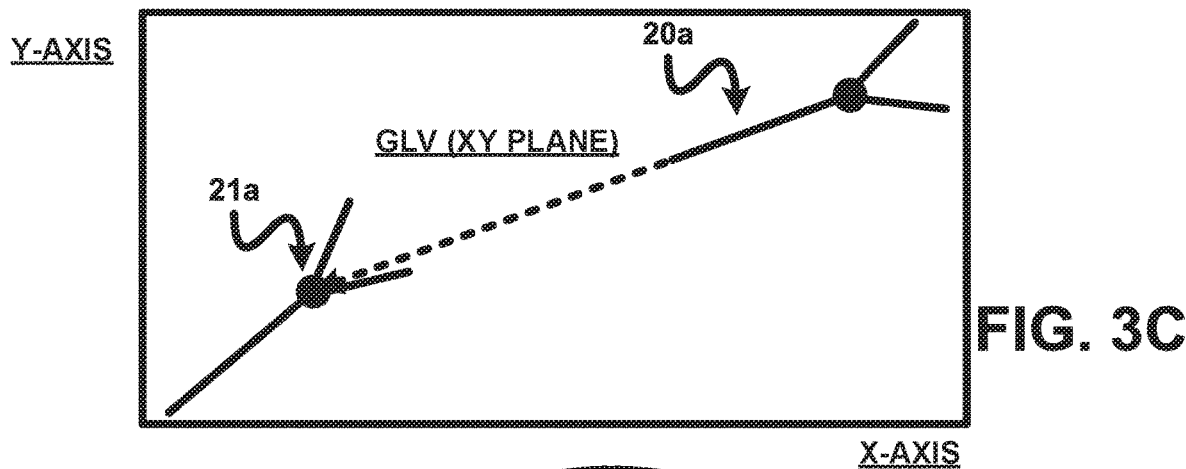

By further example, FIG. 3C illustrates an automatic motion control of dependent surgical robotic arm 21a maintaining a spatial distance, fixed or variable, between the surgical robotic arms 20a and 21a equal to the magnitude of geometric linear vector GLV with the direction of geometric linear vector GLV traversing an XY plane of coordinate space CS. For this example, automatic motion control of dependent surgical robotic arm 21a involves an orientation of dependent surgical robotic arm 21a within coordinate space CS that is independent upon an orientation of independent surgical robotic arm 20a within coordinate space CS.

Figure 3D:
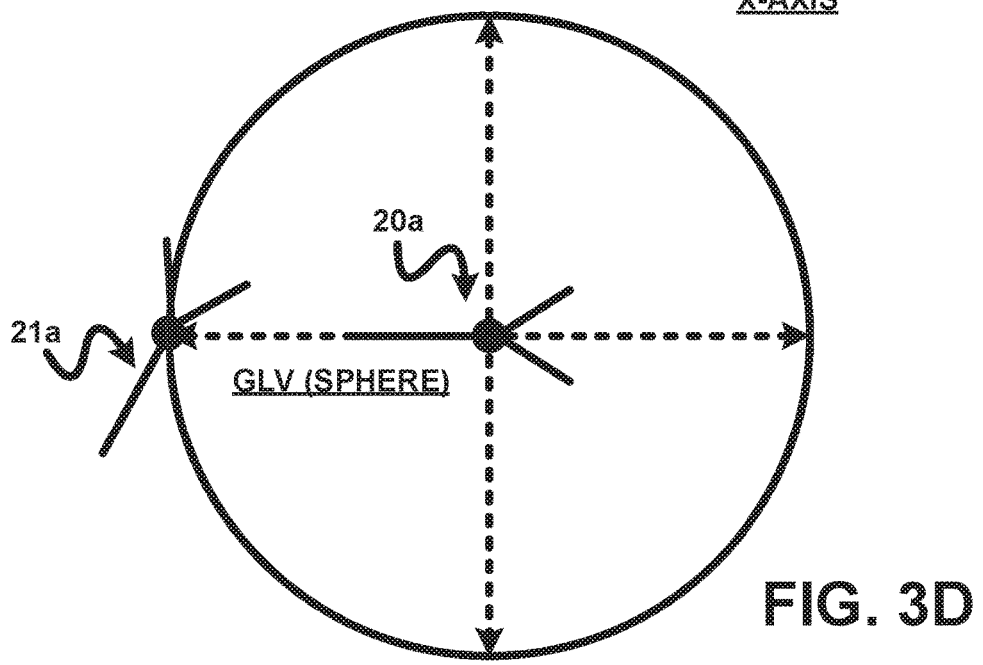

By further example, FIG. 3D illustrates an automatic motion control of dependent surgical robotic arm 21a maintaining a spatial distance, fixed or variable, between the surgical robotic arms 20a and 21a equal to the magnitude of geometric linear vector GLV radially extending from a center of a sphere with the direction of geometric linear vector GLV along a surface of the sphere being dependent upon a rotational motion of independent surgical robotic arm 20a. For this example, automatic motion control of dependent surgical robotic arm 21a involves an orientation of dependent surgical robotic arm 21a within coordinate space CS that is independent upon an orientation of independent surgical robotic arm 20a within coordinate space CS.

Figure 4A:
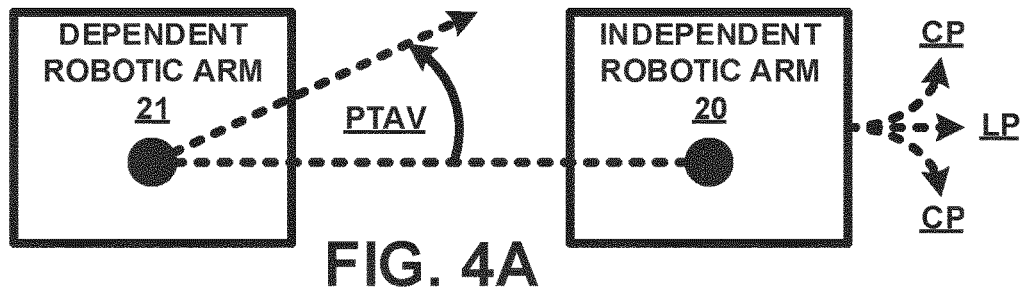
FIGS. 4A-4C illustrate exemplary embodiments of an angular orientation of an independent surgical robotic arm and a dependent surgical robotic arm in accordance with the inventive principles of the present disclosure.

Referring to FIG. 4A, a path trailing angular vector PTAV between surgical robotic arms 20 and 21 defines a spatial geometric relationship SGR whereby an automatic motion control of dependent surgical robotic arm 21 maintains an angular orientation of paths of surgical robotic arms 20 and 21 as dependent surgical robotic arm 21 trails independent surgical robotic arm 20 within coordinate space CS as controlled by an operator of the input device(s) (e.g., handle(s), joystick(s), roller ball(s), etc.).

In practice, while a direction of path trailing angular vector PTAV is variable in dependence of the motion of independent surgical robotic arm 20 within coordinate system, a magnitude of path trailing angular vector PTAV may be fixed or variable under specific condition(s). For example, the magnitude of path trailing angular vector PTAV may be reduced as surgical robotic arms 20 and 21 approach a targeted position within coordinate space CS or may attenuate over time as surgical robotic arms 20 and 21 are translated, rotated and/or pivoted within coordinate space CS.

Also in practice, for an implementation of path trailing angular vector PTAV, an orientation of dependent surgical robotic arm 21 within coordinate space CS may be dependent upon or independent of an orientation of independent surgical robotic arm 20 within coordinate space CS.

Figure 4B:
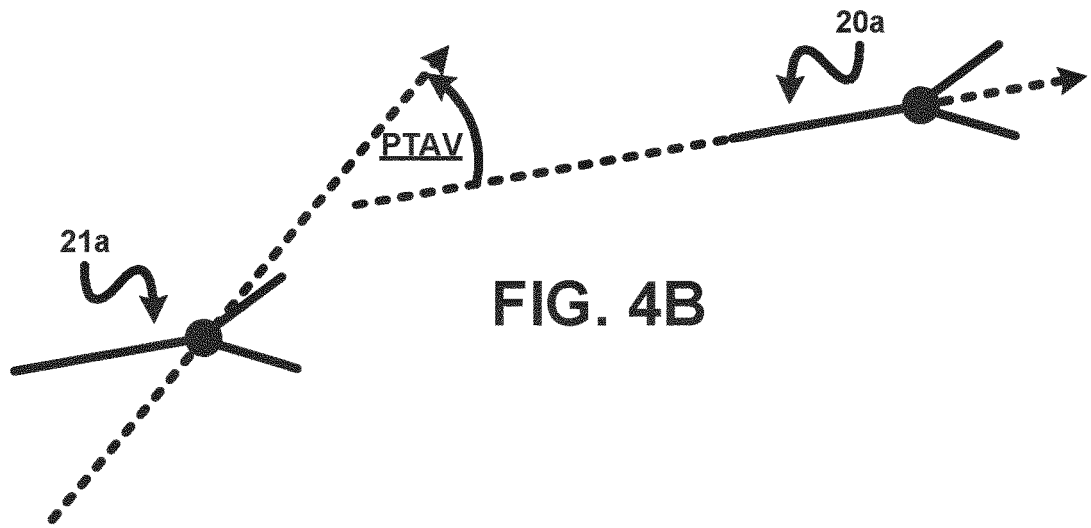
Figure 4C:
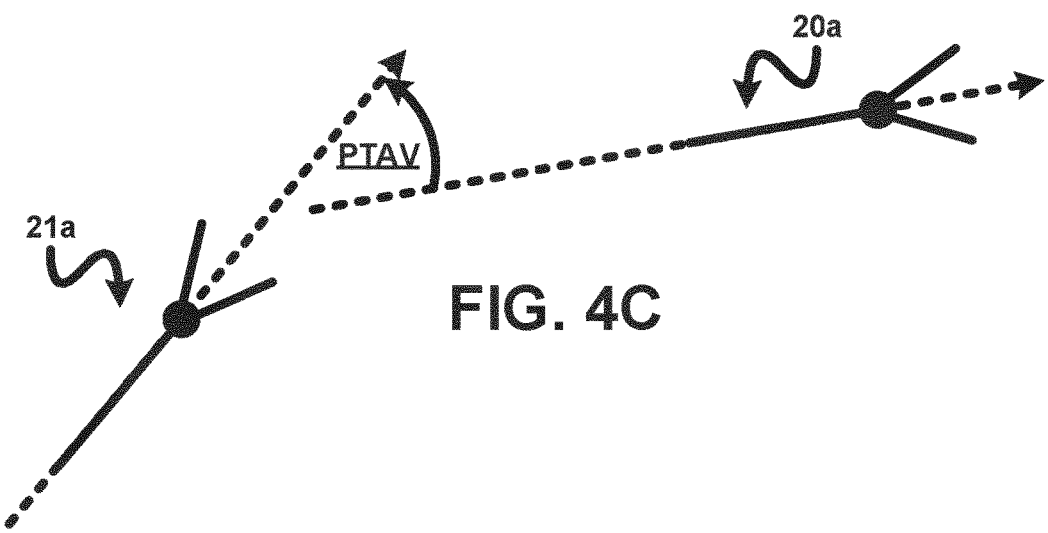

For example, FIGS. 4B and 4C illustrate an automatic motion control of dependent surgical robotic arm 21 maintaining an angular orientation, fixed or variable, of paths of surgical robotic arms 20 and 21 as dependent surgical robotic arm 21 trails independent surgical robotic arm 20 within coordinate space CS as controlled by an operator of the input device(s) (e.g., handle(s), joystick(s), roller ball(s), etc.). For FIG. 4B, an orientation of dependent surgical robotic arm 21a within coordinate space CS is dependent upon an orientation of independent surgical robotic arm 20a within coordinate space CS. Conversely, for FIG. 4C, an orientation of dependent surgical robotic arm 21a within coordinate space CS is independent of an orientation of independent surgical robotic arm 20a within coordinate space CS.

Figure 5A:
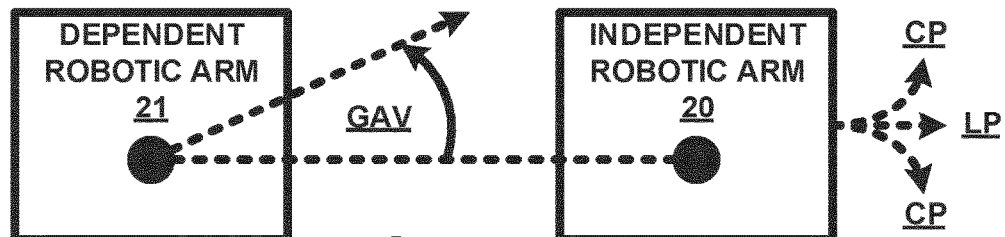
FIGS. 5A-5C illustrate additional exemplary embodiment of an angular orientation between an independent surgical robotic arm and a dependent surgical robotic arm in accordance with the inventive principles of the present disclosure.

Referring to FIG. 5A, a geometric angular vector GAV between surgical robotic arms 20 and 21 defines a spatial geometric relationship SGR whereby an automatic motion control of dependent surgical robotic arm 21 maintains an angular orientation of the paths of surgical robotic arms 20 and 21 relative to a plane of coordinate system CS as an operator of the input device(s) exercises motion control of independent surgical robotic arm 20 within coordinate space CS.

In practice, while a direction of geometric angular vector GAV is variable in dependence of the motion of independent surgical robotic arm 20 within coordinate system, a magnitude of geometric angular vector GAV may be fixed or variable under specific condition(s). For example, the magnitude of geometric angular vector GAV may be reduced as surgical robotic arms 20 and 21 approach a targeted position within coordinate space CS or may attenuate over time as surgical robotic arms 20 and 21 are translated, rotated and/or pivoted within coordinate space CS.

Also in practice, for an implementation of geometric angular vector GAV, an orientation of dependent surgical robotic arm 21 within coordinate space CS may be dependent upon or independent of an orientation of independent surgical robotic arm 20 within coordinate space CS.

Figure 5B:
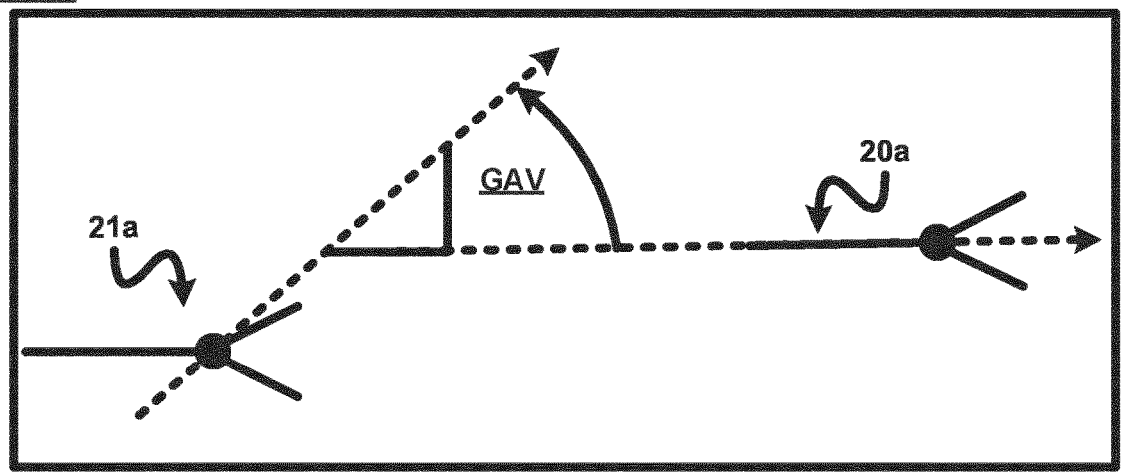
Figure 5C:
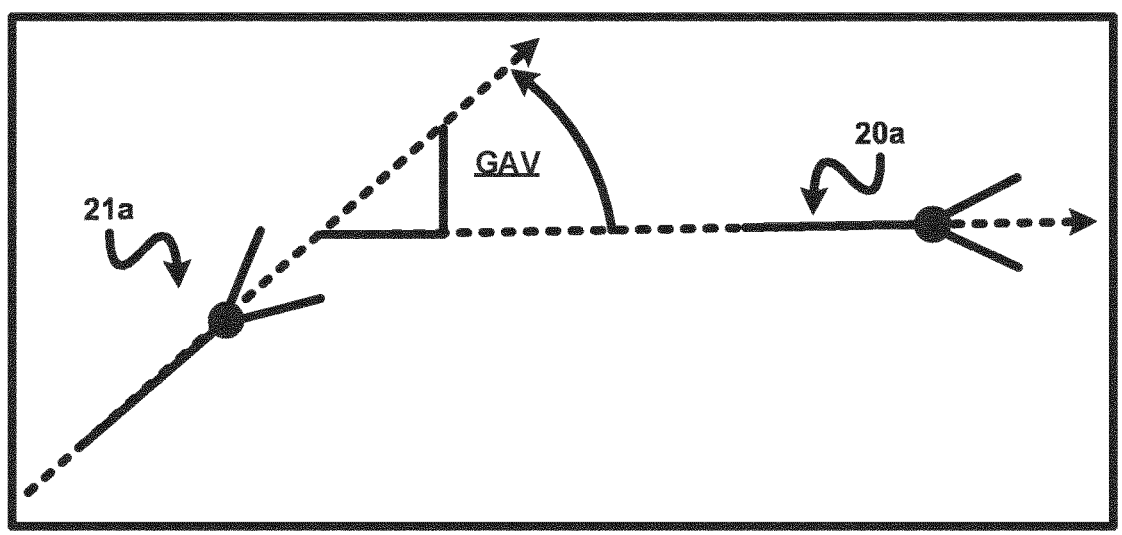

For example, FIGS. 5B and 5C illustrate an automatic motion control of dependent surgical robotic arm 21 maintaining an angular orientation, fixed or variable, of the paths of surgical robotic arms 20 and 21 relative to an XY plane as dependent surgical robotic arm 21 trails independent surgical robotic arm 20 within coordinate space CS as controlled by an operator of the input device(s) (e.g., handle(s), joystick(s), roller ball(s), etc.). For FIG. 5B, an orientation of dependent surgical robotic arm 21a within coordinate space CS is dependent upon an orientation of independent surgical robotic arm 20a within coordinate space CS. Conversely, for FIG. 5C, an orientation of dependent surgical robotic arm 21a within coordinate space CS is independent of an orientation of independent surgical robotic arm 20a within coordinate space CS.

Referring to FIG. 6A, a procedural synchronization 23 between surgical robotic arms 20 and 21 defines a spatial geometric relationship of the present disclosure derived from an implementation of a surgical task (e.g., a laparoscopic knot tying) whereby an automatic motion control of dependent surgical robotic arm 21 within the coordinate space CS is a function within the context of the surgical task of a motion of independent surgical robotic arm 20 within the coordinate space CS as an operator of the input device(s) exercises motion control of independent surgical robotic arm 20 within coordinate space CS in accordance with the surgical task.

In practice, the automatic motion control of dependent surgical robotic arm 21 may be computed via an explicit function 24 defining the procedural relationship between surgical robotic arms 20 and 21 in accordance with the surgical task.

Also in practice, the automatic motion control of dependent surgical robotic arm 21 may be retrieved via a lookup table 25 storing the procedural relationship between surgical robotic arms 20 and 21 in accordance with the surgical task.

For example, FIGS. 6B-6G illustrate sequential steps of a laparoscopic knot tying performed by surgical robotic arms 20a and 21a.

In one embodiment, the automatic motion control of dependent surgical robotic arm 21a may be computed via explicit function defining the procedural relationship between surgical robotic arms 20a and 21a in accordance with the steps of the laparoscopic knot tying task. More particularly for this example, an explicit function may define a motion of dependent surgical robotic arm 21a relative to a positioning of independent surgical robotic arm 20a upon a completion of a rotation of independent surgical robotic arm 20a wrapping a thread around independent surgical robotic arm 20a as shown in FIG. 6C whereby dependent surgical robotic arm 21a is automatically moved in a position relative to independent surgical robotic arm 20a to thereby grasp the thread as shown FIG. 6D. Furthermore, an additional explicit function may define a motion of dependent surgical robotic arm 21a relative to a positioning of independent surgical robotic arm 20a upon a completion of a motion of independent surgical robotic arm 20a through the looped thread as shown in FIGS. 6D and 6E whereby dependent surgical robotic arm 21a is automatically moved in a position relative to independent surgical robotic arm 20a to thereby tightened the thread as shown in FIG. 6G.

Alternatively, a lookup table may define a motion of dependent surgical robotic arm 21a relative to a positioning of independent surgical robotic arm 20a upon a completion of a rotation of independent surgical robotic arm 20a wrapping a thread around independent surgical robotic arm 20a as shown in FIG. 6C whereby dependent surgical robotic arm 21a is automatically moved in a position relative to independent surgical robotic arm 20a to thereby grasp the thread as shown FIG. 6D. Furthermore, the lookup table may define a motion of dependent surgical robotic arm 21a relative to a positioning of independent surgical robotic arm 20a upon a completion of a motion of independent surgical robotic arm 20a through the looped thread as shown in FIGS. 6D and 6E whereby dependent surgical robotic arm 21a is automatically moved in a position relative to independent surgical robotic arm 20a to thereby tightened the thread as shown in FIG. 6G.

Figure 7:
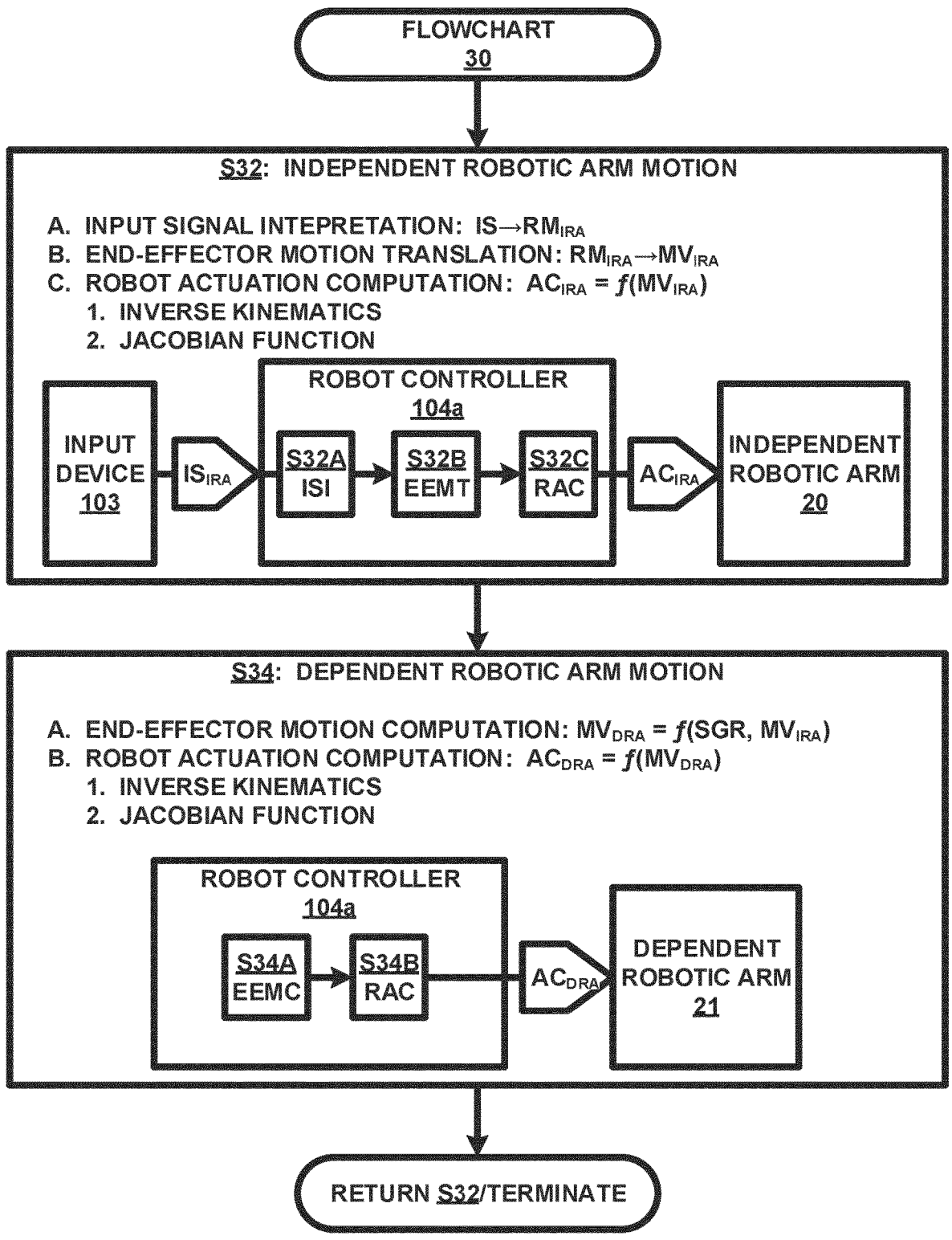
FIG. 7 illustrates a flowchart representative of a first exemplary embodiment of a motion dependency robot control method for an independent surgical robotic arm and a dependent surgical robotic arm in accordance with the inventive principles of the present disclosure.
Figure 8A:
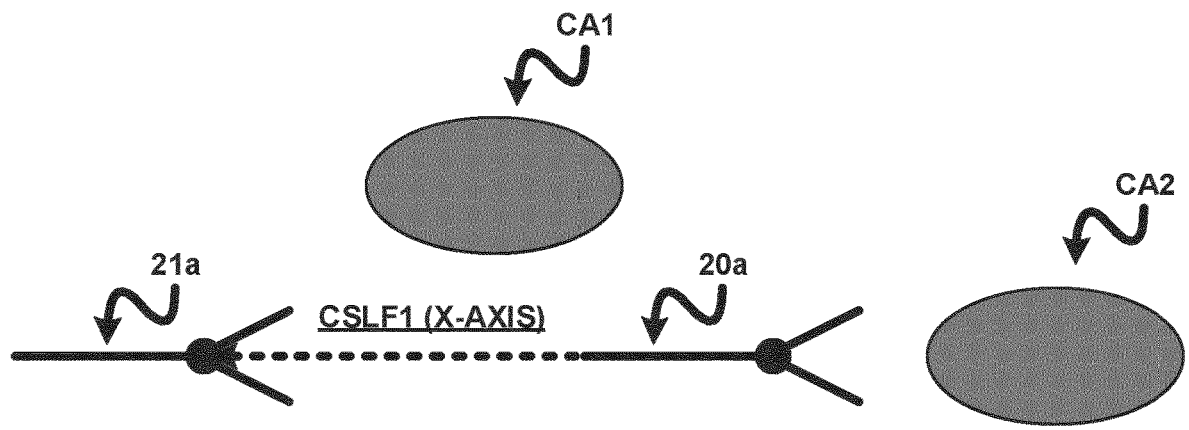
FIGS. 8A-8B illustrate exemplary embodiments of an obstacle avoidance by a dependent surgical robotic arm in accordance with the inventive principles of the present disclosure.
Figure 8B:
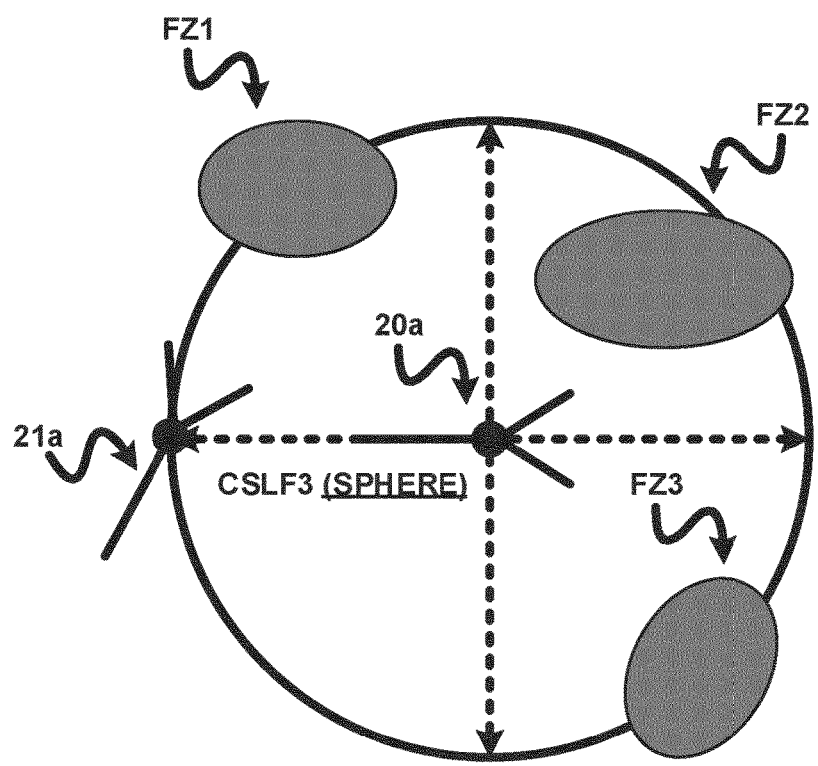
Figure 9:
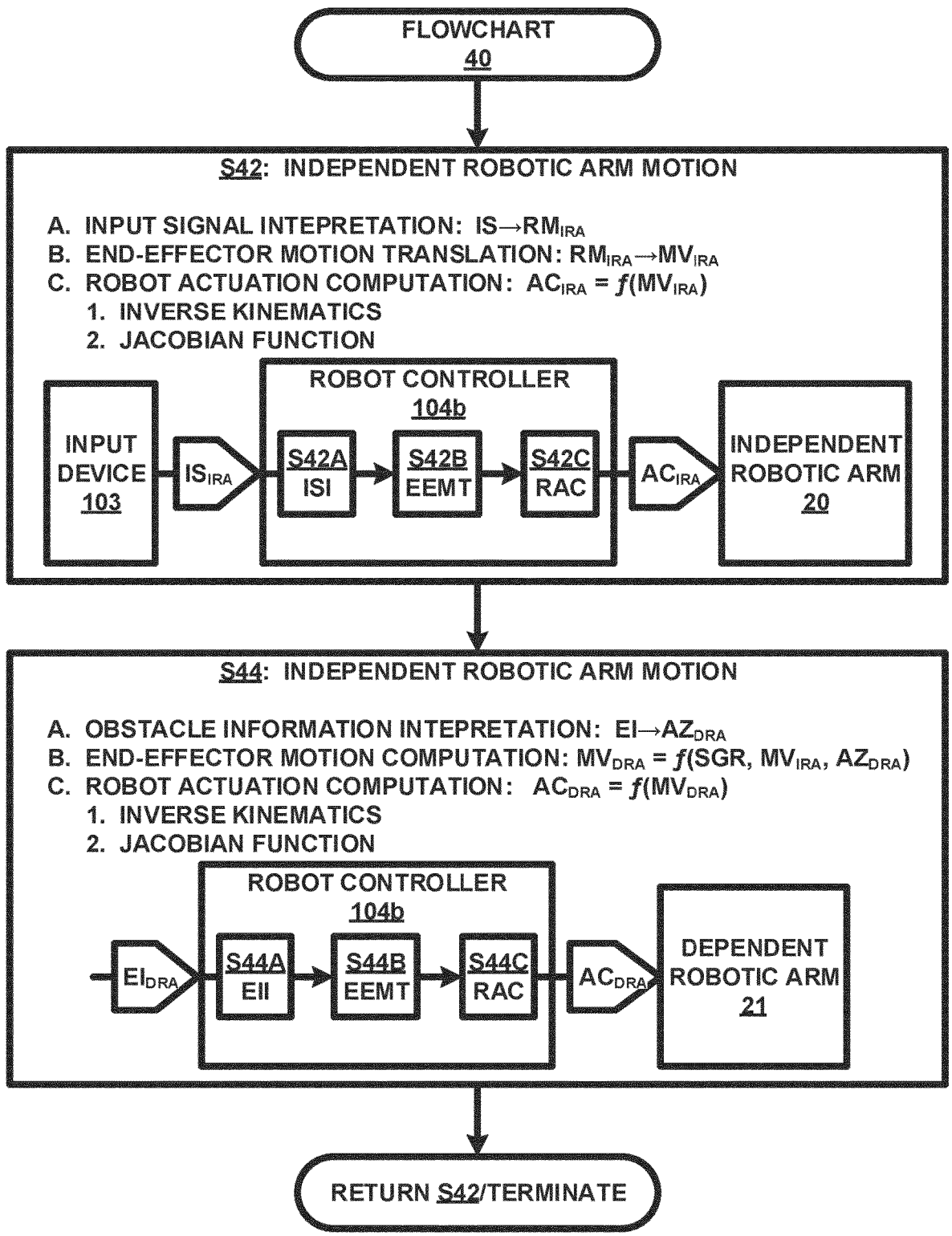
FIG. 9 illustrates a flowchart representative of a second exemplary embodiment of a motion dependency robot control method for an independent surgical robotic arm and a dependent surgical robotic arm in accordance with the inventive principles of the present disclosure.

To further facilitate an understanding of the inventions of the present disclosure, the following description of FIGS. 7-9 teaches basic inventive principles of motion dependency robot control method for an independent surgical robotic arm and a dependent surgical robotic arm in accordance with the inventive principles of the present disclosure. From this description of FIGS. 7-9, those having ordinary skill in the art will appreciate how to apply the inventive principles of the present disclosure to practice numerous and various of motion dependency robot control method for an independent surgical robotic arm and one or more dependent surgical robotic arms.

Referring to FIG. 7, a flowchart 30 represents a motion dependency robot control method for independent surgical robotic arm 20 (FIG. 1) and dependent surgical robotic arm 21 (FIG. 1).

A stage S32 of flowchart 30 encompasses an independent surgical robotic arm motion within coordinate space CS (FIG. 1) involving:

A. an interpretation as known in the art of the present disclosure of an input signal IS directing a robot motion $RM_{IRA}$ of independent surgical robotic arm 20 within coordinate space CS in terms of a translation motion, a rotational motion and/or a pivoting motion of independent surgical robotic arm 20;

B. a translation as known in the art of the present disclosure of robot motion $RM_{IRA}$ into a motion vector $MV_{IRA}$ representing a targeted positioning or a targeted velocity of an end-effector of independent surgical robotic arm 20 within coordinate space CS; and C. a computation as known in the art of the present disclosure of actuation commands $AC_{IRA}$ for actuator(s) of independent surgical robotic arm 20 (e.g., actuatable joints) to thereby move the end-effector of independent surgical robotic arm 20 to the targeted position or at the targeted velocity within coordinate space CS.

In practice, an inverse kinematics model may be used to compute actuation commands $AC_{IRA}$ of each actuator of independent surgical robotic arm 20 to translate, rotate and/or pivot independent arm 20 from a current position to a targeted position within coordinate space CS.

Also in practice, a Jacobian function may be used to compute actuation commands $AC_{IRA}$ of each actuator of independent surgical robotic arm 20 to translate, rotate and/or pivot independent surgical robotic arm 20 at a targeted velocity within coordinate space CS.

An exemplary execution of stage S32 as shown in FIG. 7 encompasses an input device 103 (e.g., handle(s), joystick(s), roller ball(s), etc.) communicating an input signal $IS_{IRA}$ to a motion dependency robot controller 104a of the present disclosure, which computes actuation commands $AC_{IRA}$ as previously described for stage S32 to thereby control an independent motion of independent surgical robotic arm 20.

Upon completion of the end-effector motion translation of stage S32, a stage S34 of flowchart 30 encompasses a dependent surgical robotic arm motion within coordinate space CS (FIG. 1) involving:

A. a computation of a motion vector $MV_{DR}A$ representing a targeted positioning or a targeted velocity of an end-effector of dependent surgical robotic arm 21 within coordinate space CS whereby the motion vector $MV_{DRA}$ is a function of motion vector $MV_{IRA}$ for independent surgical robotic arm 20 and any applicable spatial geometric relationship (e.g., one of the spatial geometric relationships of FIGS. 2-6); and B. a computation as known in the art of the present disclosure of actuation commands $AC_{DRA}$ for actuator(s) of dependent surgical robotic arm 21 (e.g., actuatable joints) to thereby move the end-effector of dependent surgical robotic arm 21 to the targeted position or at a targeted velocity within coordinate space CS.

In practice, an inverse kinematics model may be used to compute actuation commands $AC_{DRA}$ of each actuator of dependent surgical robotic arm 21 to translate, rotate and/or pivot dependent surgical robotic arm 21 from a current position to a targeted position within coordinate space CS.

Also in practice, a Jacobian function may be used to compute actuation commands $AC_{DRA}$ of each actuator of dependent surgical robotic arm 21 to translate, rotate and/or pivot independent surgical robotic arm 21 at a targeted velocity within coordinate space CS.

An exemplary execution of stage S34 as shown in FIG. 7 encompasses motion dependency robot controller 104a computing actuation commands $AC_{DRA}$ as previously described for stage S34 to thereby control a motion of dependent surgical robotic arm 21 within coordinate space CS dependent upon the motion of independent surgical robotic arm 20 within coordinate space CS.

In practice, while controlling a motion of dependent surgical robotic arm 21 within coordinate space CS dependent upon the motion of independent surgical robotic arm 20 within coordinate space CS, a motion dependency robot controller of the present disclosure may implement an obstacle avoidance of environmental hazards.

For example, FIG. 8A illustrates collision areas CA1 and CA2 representative of staffers, devices and/or sensors in the operation room within an operating room. For surgical robotic arms 20a and 21a to avoid collision areas CA1 and CA2, an input device of the surgical robotic system is operated to control of a motion of independent surgical robotic arm 21a in avoidance of collision areas CA1 and CA, while a motion dependency robot controller of the present disclosure processes environmental information indicative of a location of collision areas CA1 and CA2 and modifies the dependent motion of dependent surgical robotic arm 21a as necessary to avoid collision areas CA1 and CA2. The environment information in this case may be provided by a tracking system registered to the surgical robot system (e.g., an electromagnetic tracking system or an optical tracking system).

By further example, FIG. 8B illustrates anatomical forbidden zones FZ1-FZ3 relative to a sphere for controlling the motion of dependent surgical robotic arm 21a dependent upon the motion of independent surgical robotic arm 20a. A motion dependency robot controller of the present disclosure processes information indicative of a location of anatomical forbidden zones FZ1-FZ3 and modifies the dependent motion of dependent surgical robotic arm 21a as necessary to avoid anatomical forbidden zones FZ1-FZ3. The environmental information in this case may be derived from image(s) of the anatomical region illustrating anatomical forbidden zones FZ1-FZ3 as delineated within the image(s) (e.g., a fusion of intraoperative and preoperative images or an endoscopic image).

More particularly, if a constant distance is to be maintained between the surgical robotic arms 20a and 21a on the surface of a sphere as shown in FIG. 8B, then a position of dependent surgical robotic arm 21a may be anywhere on the sphere. Thus, if the environment signal is an endoscopic video, then the operator can mark allowed (or forbidden) zones on the image. Consequently, as independent surgical robotic arm 20a is moving, motion dependency robot controller of the present disclosure tracks the allowed zone(s) in the image and computes the sections on the surface of the sphere where the dependent surgical robotic arm 21a is allowed.

Referring to FIG. 9, a flowchart 40 represents a motion dependency robot control method for independent surgical robotic arm 20 (FIG. 1) and dependent surgical robotic arm 21 (FIG. 1) incorporating an obstacle avoidance aspect. Specifically, flowchart 40 is a modified version of flowchart 30 (FIG. 7) as previously described herein with a stage S42 of flowchart 40 corresponding to stage S32 of flowchart 30, and a stage S44 of flowchart 40 corresponding to stage S34 of flowchart 30 with a motion dependency robot controller 104b of the present disclosure executing additional acts of:

A. an interpretation as known in the art of the present disclosure of an environmental signal $ES_{DRA}$ to yield allowed zones $AZ_{DRA}$ within coordinate space CS; and B. a computation of a motion vector $MV_{DRA}$ representing a targeted positioning or a targeted velocity of an end-effector of dependent surgical robotic arm 21 within coordinate space CS whereby the motion vector $MV_{DRA}$ is a function of motion vector $MV_{IRA}$ for independent surgical robotic arm 20, any applicable spatial geometric relationship (e.g., one of the spatial geometric relationships of FIGS. 2-6) and the allowed zones $AZ_{DRA}$.

To facilitate a further understanding of the inventions of the present disclosure, the following description of FIGS. 10-13 teaches basic inventive principles of a spatial geometric relationship between a pair of independent surgical robotic arms and a dependent surgical robotic arm in accordance with the inventive principles of the present disclosure. From this description of FIGS. 10-13, those having ordinary skill in the art will appreciate how to apply the inventive principles of the present disclosure to practice numerous and various spatial geometric relationships between a pair of independent surgical robotic arms and a dependent surgical robotic arm.

Referring to FIG. 10, again, the three-dimensional ("3D") coordinate space CS, symbolized by the X-Y axes as shown for clarity, represents an operating space for performing a surgical robotic procedure (e.g., general surgical procedures, cardiac surgical procedures, neurosurgery, etc.). In practice, coordinate space CS may be established by a support of an anatomical region of a patient within the operating space (e.g., a patient table).

A motion vector $MV_{IRA}$ of an independent surgical robotic arms 20 and 22 within coordinate space CS is controllable as known in the art of the present disclosure by an input device of a surgical robot system (not shown) (e.g., handle(s), joystick(s), roller ball(s), etc.). More particularly, the motion vectors $MV_{IRA1}$ and $MV_{IRA2}$ of an independent surgical robotic arms 20 and 22 within coordinate space CS is a function of an input signals $IS_{IRA1}$ and $IS_{IRA2}$ generated by input device(s) directing a translation, a rotation and/or a pivoting of independent surgical robotic arms 20 and 22 within coordinate space CS. In practice, the input device may be switchable between a motion control of surgical robotic arms 20 and 22 within coordinate space CS, or alternatively, two separate input devices may be employed to independently control a motion of surgical robotic arms 20 and 22 within coordinate space CS A translation, a rotation and/or a pivoting of a dependent surgical robotic arm 21 within coordinate space CS is automatically controlled by a spatial geometrical relationship SGR of the present disclosure between independent surgical robotic arms 20 and 22 and dependent surgical robotic arm 21. More particularly, a motion vector $MV_{DRA}$ of dependent surgical robotic arm 21 within coordinate space CS is a function of motion vector $MV_{IRA1}$ of an independent surgical robotic arm 20 and motion vector $MV_{IRA2}$ of an independent surgical robotic arm 22 within coordinate space CS in the context of the spatial geometrical relationship SGR to thereby automatically control a translation, a rotation and/or a pivoting of dependent surgical robotic arm 21 within coordinate space CS.

In practice, the motion vector $MV_{IRA}$ of independent surgical robotic arm 21, the motion vector $MV_{IRA2}$ of independent surgical robotic arm 21 and the motion vector $MV_{DRA}$ of dependent surgical robotic arm 21 may be derived as targeted positions of surgical robotic arms 20-22 within coordinate system CS as previously described herein.

Also in practice, the motion vector $MV_{IRA1}$ of independent surgical robotic arm 20, the motion vector $MV_{IRA2}$ of independent surgical robotic arm 22, and the motion vector $MV_{DRA}$ of dependent surgical robotic arm 21 may be derived as targeted velocities of a current orientation of surgical robotic arms 20-22 within coordinate system CS.

The spatial geometric relationship SGR is a motion dependency of dependent surgical robotic arm 21 on an operator controlled motion of independent surgical robotic arms 20 and 22 within coordinate space CS. More particularly, the spatial geometric relationship SGR defines a motion vector in the form of a linear vector and/or an angular vector, and may be further defined by a magnitude and/or a direction of the motion vector relative to an axis or a plane within the coordinate space or to a geometric object within the coordinate space.

In practice, a spatial geometric relationship SGR between surgical robotic arms 20 and 21 and a different spatial geometric relationship SGR between surgical robotic arms 21 and 22 may be concurrently implemented by a motion dependency robot controller of the present invention (e.g., the spatial geometric relationship SGR of FIGS. 2-6).

Alternatively in practice, a single spatial geometric relationship SGR between surgical robotic arms 20-22 may be implemented by a motion dependency robot controller of the present invention.

Figure 11:
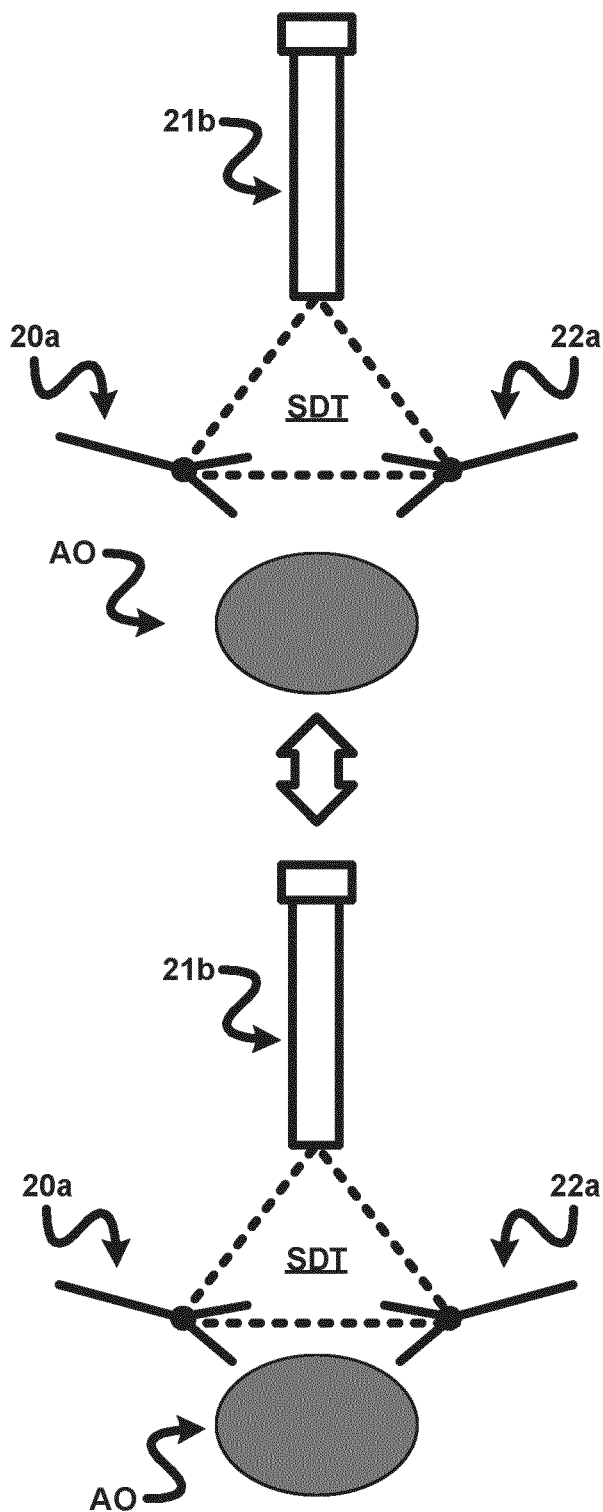
FIG. 11 illustrates an exemplary embodiment of a relative positioning between a pair of independent surgical robotic arms and a dependent surgical robotic arm in accordance with the inventive principles of the present disclosure.

The following description of FIG. 11 illustrates an example of spatial geometric relationship SGR between surgical robotic arms 20-22.

Referring to FIG. 11, a spatial distance triangle SDT defines a spatial geometric relationship between surgical robotic arms 20-22 for maintaining a spatial distance between an endoscopic dependent surgical robotic arm 21b and independent surgical robotic arms 20a and 22a as independent surgical robotic arms 20a and 22a are moved in towards or away form an anatomical object AO.

Figure 12:
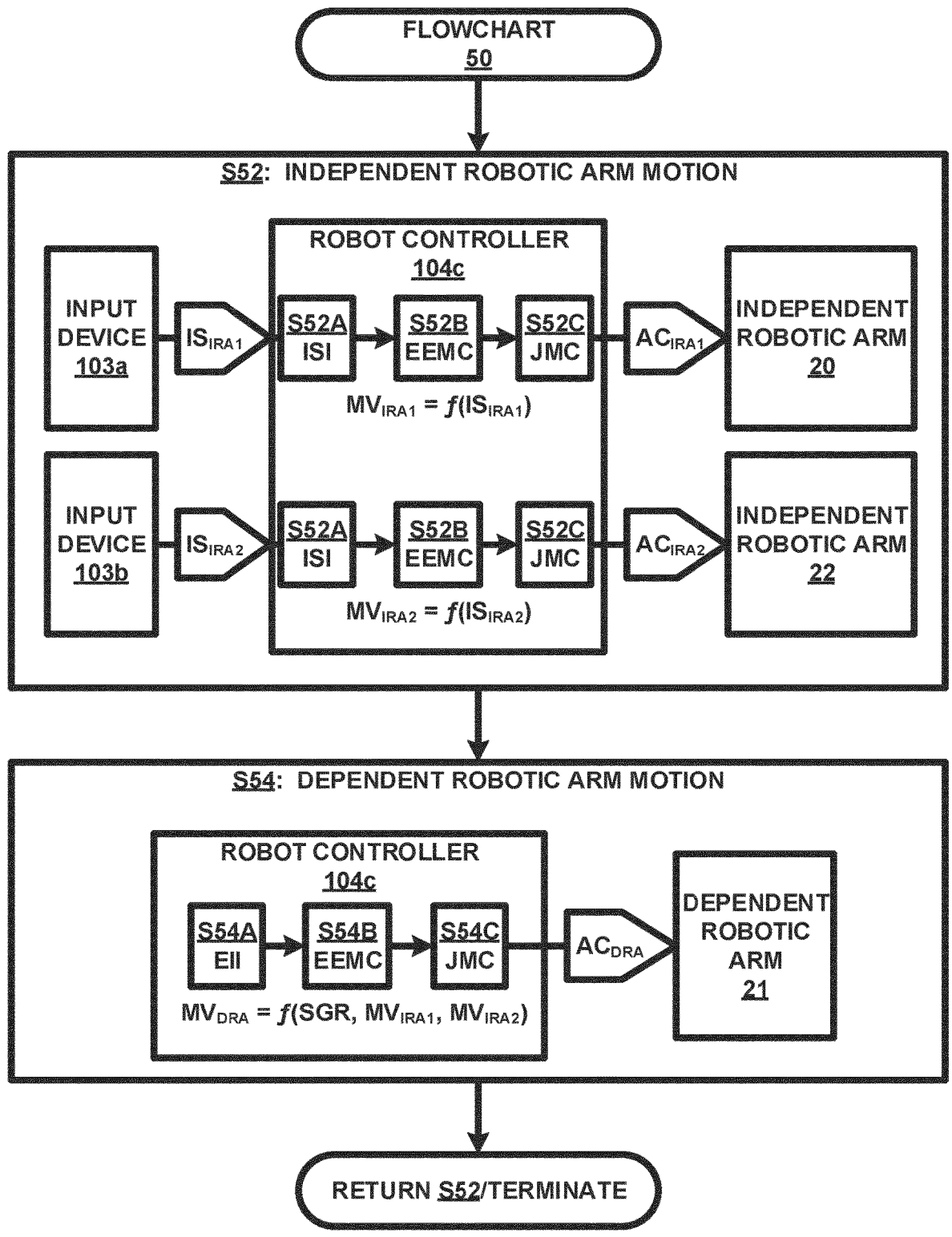
FIG. 12 illustrates a flowchart representative of a first exemplary embodiment of a motion dependency robot control method for a pair of independent surgical robotic arms and a dependent surgical robotic arm in accordance with the inventive principles of the present disclosure.

Referring to FIG. 12, a flowchart 50 represents a motion dependency robot control method for independent surgical robotic arms 20 and 22 (FIG. 10) and dependent surgical robotic arm 21 (FIG. 10). Specifically, flowchart 50 is a modified version of flowchart 30 (FIG. 7) as previously described herein with a stage S52 of flowchart 50 corresponding to stage S32 of flowchart 30, and a stage S54 of flowchart 50 corresponding to stage S34 of flowchart 30 with a motion dependency robot controller 104c of the present disclosure computing a motion vector $MV_{DRA}$ representing a targeted positioning or a targeted velocity of an end-effector of dependent surgical robotic arm 21 within coordinate space CS whereby the motion vector $MV_{DRA}$ is a function of motion vector $MV_{IRA}$ for independent surgical robotic arm 20, motion vector $MV_{IRA2}$ for independent surgical robotic arm 22, and any applicable spatial geometric relationships (e.g., one of the spatial geometric relationships of FIGS. 2-6 and 11).

Figure 13:
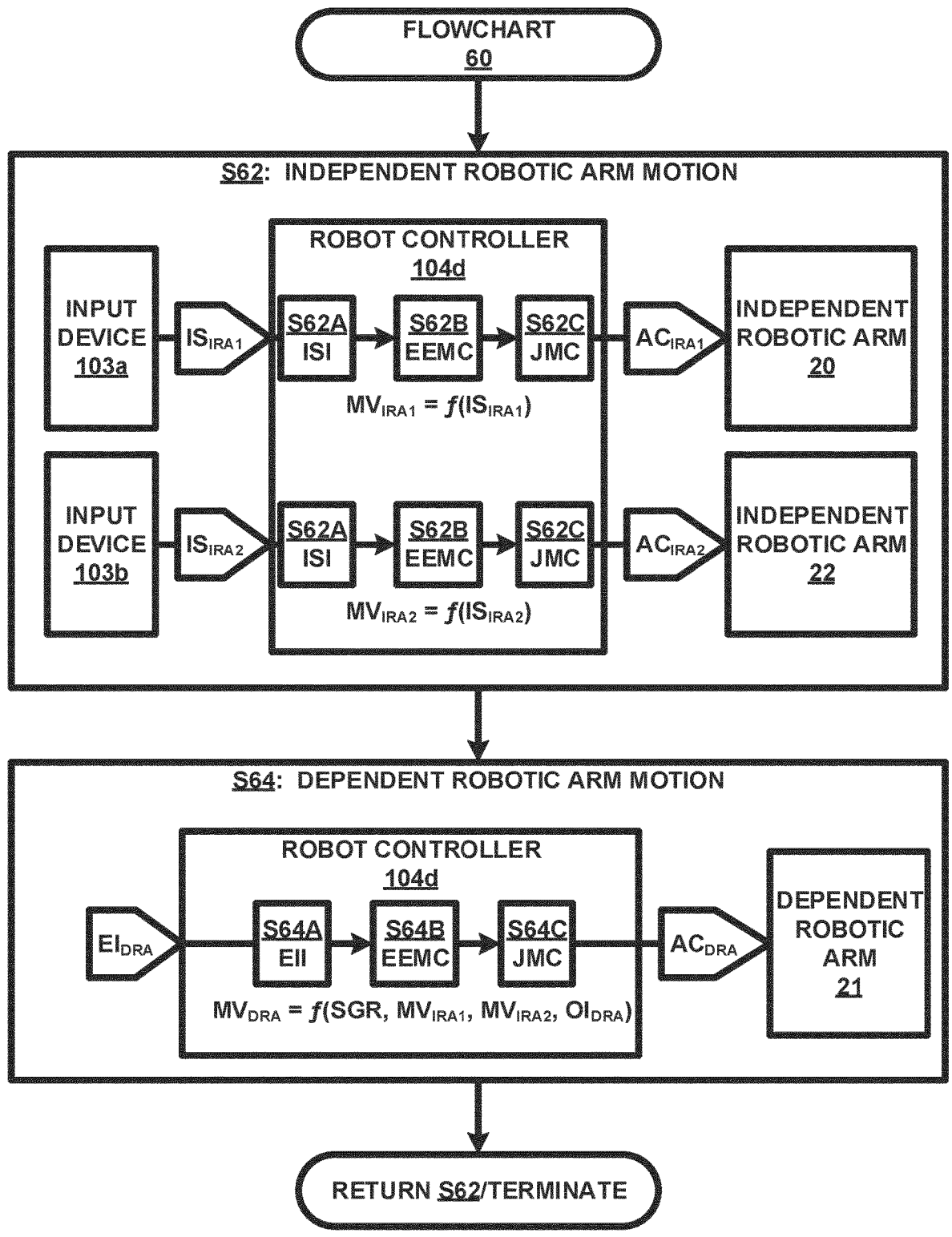
FIG. 13 illustrates a flowchart representative of a second exemplary embodiment of a motion dependency robot control method for a pair of independent surgical robotic arms and a dependent surgical robotic arm in accordance with the inventive principles of the present disclosure.

Referring to FIG. 13, a flowchart 50 represents a motion dependency robot control method for independent surgical robotic arms 20 and 22 (FIG. 10) and dependent surgical robotic arm 21 (FIG. 10) incorporating an obstacle avoidance aspect. Specifically, flowchart 60 is a modified version of flowchart 40 (FIG. 9) as previously described herein with a stage S62 of flowchart 60 corresponding to stage S42 of flowchart 40, and a stage S64 of flowchart 60 corresponding to stage S44 of flowchart 40 with a motion dependency robot controller 104d of the present disclosure computing a motion vector $MV_{DRA}$ representing a targeted positioning or a targeted velocity of an end-effector of dependent surgical robotic arm 21 within coordinate space CS whereby the motion vector $MV_{DRA}$ is a function of motion vector $MV_{IRA1}$ for independent surgical robotic arm 20, motion vector $MV_{IRA2}$ for independent surgical robotic arm 22, any applicable spatial geometric relationships (e.g., one of the spatial geometric relationships of FIGS. 2-6 and 11), and allowable zones AZ.

To facilitate a further understanding of the inventions of the present disclosure, the following description of FIGS. 14-16 teaches basic inventive principles of motion dependency surgical robotic systems and motion dependency surgical robotic controllers in accordance with the inventive principles of the present disclosure. From this description of FIGS. 14-16, those having ordinary skill in the art will appreciate how to apply the inventive principles of the present disclosure to practice numerous and various embodiments of a motion dependency surgical robotic systems and a motion dependency surgical robotic controller in accordance with the inventive principles of the present disclosure.

Figure 14A:
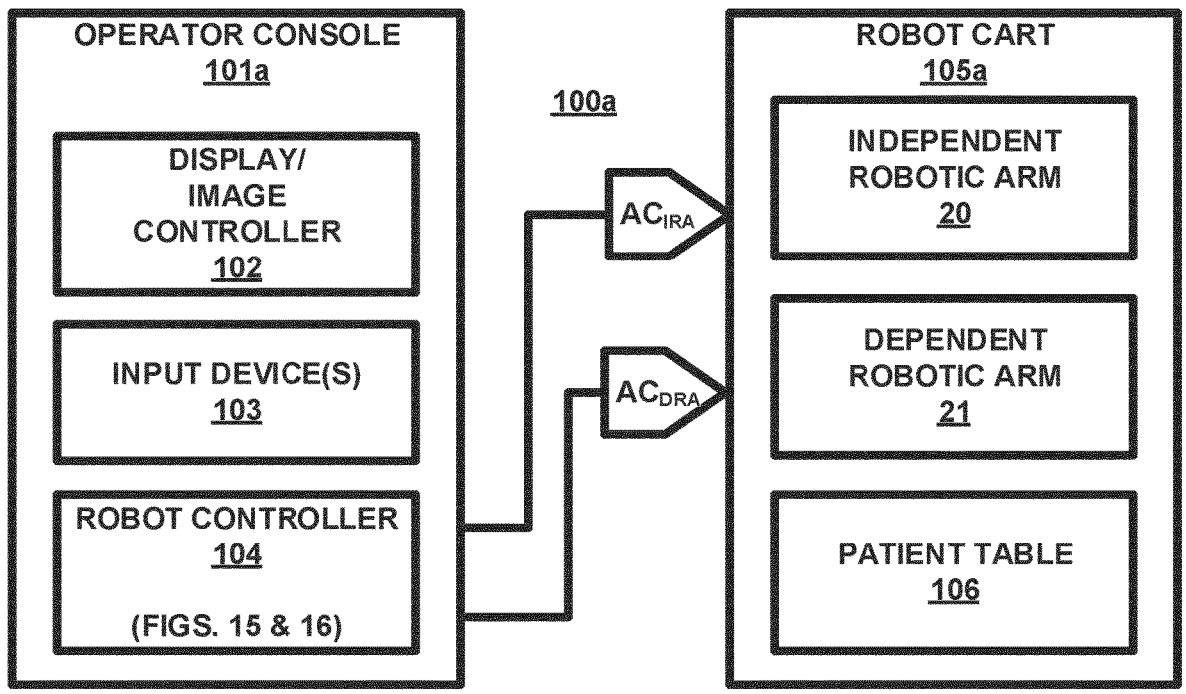
FIGS. 14A and 14B illustrate exemplary embodiments of a motion dependency surgical robot system in accordance with the inventive principles of the present disclosure.

Referring to FIG. 14A, a motion dependency surgical robotic system 100a of the present disclosure employs an operator console 101 and a robot cart 105a.

Operator console 101a includes a display/image controller 102 for displaying preoperative images, intraoperative images and/or fusion of such images as known in the art of the present disclosure.

Operator console 101a further includes one or more input device(s) 103 (e.g., handle(s), joystick(s), roller ball(s), etc.) and a motion dependency robot controller 104 as will be further described herein in connection with FIGS. 15 and 16.

Robot cart 105a includes independent surgical robotic arm 20, dependent surgical robotic arm 21, and a patient table 106.

In practice, robot cart 105a may include additional surgical robotic arms 20 and/or surgical robotic arms 21.

Also in practice, a surgical robotic arm may serve an independent surgical robotic arm or a dependent surgical robotic arm based on a particular surgical task to be performed by system 100.

Figure 14B:
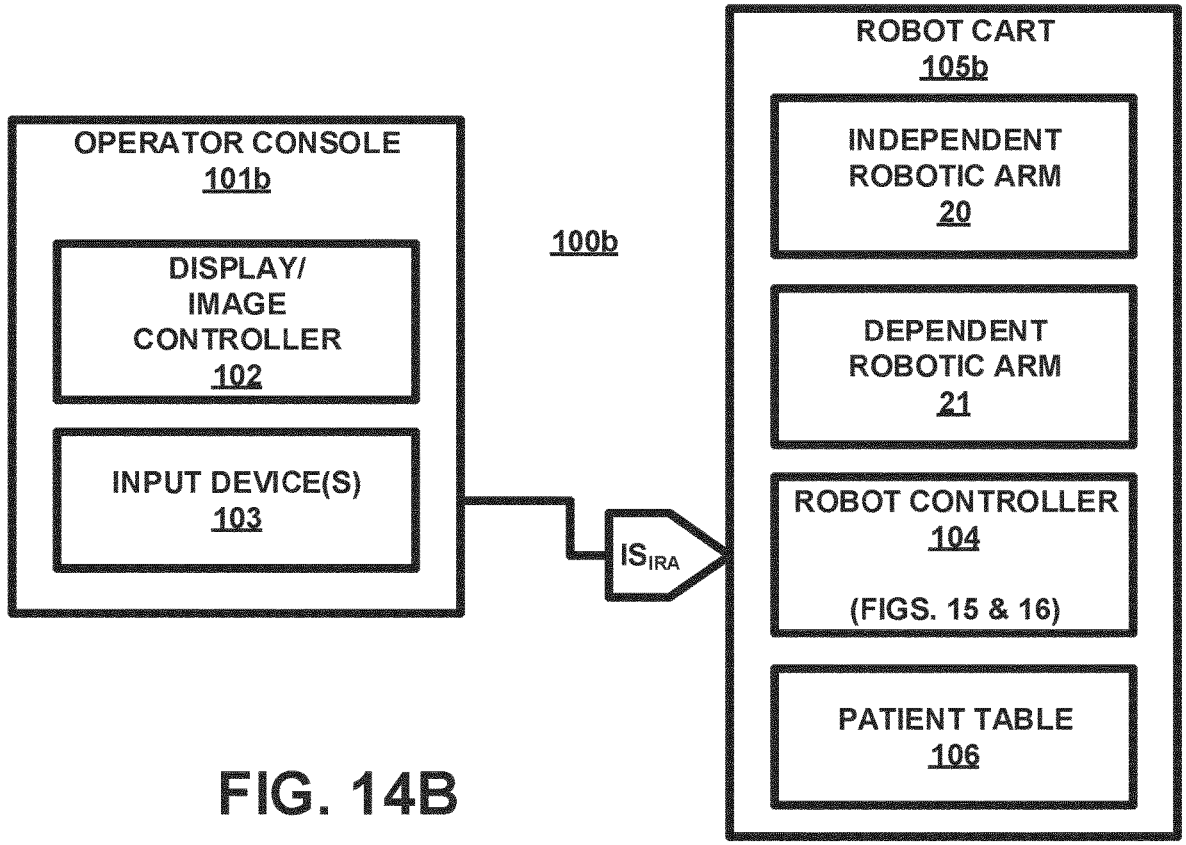

Referring to FIG. 14B, a motion dependency surgical robotic system 100b is an alternative version of system 100a (FIG. 14A) with robot cart 105b including motion dependency robot controller 104.

A motion dependency surgical robotic system of the present disclosure (e.g., systems 100a and 100b) may be practiced with an imaging system and/or a tracking system.

If employed, an imaging system implements any imaging modality, known in the art of the present disclosure and hereinafter conceived, for imaging an anatomical region (not shown) and for communicating imaging data informative of such imaging to the motion dependency surgical robotic system. Examples of the imaging modality include, but are not limited to, CT, MRI, X-ray and ultrasound.

Alternatively, the imaging system may be omitted, particularly when the motion dependency surgical robotic system employs an imaging instrument held by a surgical robotic arm for imaging the anatomical structure. Examples of such imaging instruments include, but are not limited to, an endoscope and a laparoscope.

If employed, a tracking system implements any tracking technique, known in the art of the present disclosure and hereinafter conceived, for tracking a surgical robotic arm within the coordinate space and for communicating tracking data indicative of such tracking to the motion dependency surgical robotic system. Examples of the tracking technique include, but are not limited to, electromagnetic tracking, optical tracking and Fiber-Optic RealShape ("FORS") sensor tracking.

Alternatively, the tracking system may be omitted, particularly when the motion dependency surgical robotic system employs encoded surgical robots arms generating tracking data for tracking the surgical robotic arm(s) within the coordinate space.

Exemplary embodiments of motion dependency robot controller 104 will now be described herein.

For example, motion dependency robot controller 104 may include a processor, a memory, a user interface, a network interface, and a storage interconnected via one or more system buses.

The processor may be any hardware device capable of executing instructions stored in memory or storage or otherwise processing data. As such, the processor may include a microprocessor, field programmable gate array (FPGA), application-specific integrated circuit (ASIC), or other similar devices.

The memory may include various memories such as, for example L1, L2, or L3 cache or system memory. As such, the memory may include static random access memory (SRAM), dynamic RAM (DRAM), flash memory, read only memory (ROM), or other similar memory devices.

The user interface may include one or more devices for enabling communication with a user such as an administrator. For example, the user interface may include a display, a mouse, and a keyboard for receiving user commands. In some embodiments, the user interface may include a command line interface or graphical user interface that may be presented to a remote terminal via the network interface.

The network interface may include one or more devices for enabling communication with other hardware devices. For example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent.

The storage may include one or more machine-readable storage media such as read-only memory (ROM), random-access memory (RAM), magnetic disk storage media, optical storage media, flash-memory devices, or similar storage media. In various embodiments, the storage may store instructions for execution by the processor or data upon with the processor may operate. For example, the storage may store a base operating system for controlling various basic operations of the hardware. The storage may further store application module(s) in the form of executable software/firmware and/or application module(s).

Figure 15A:
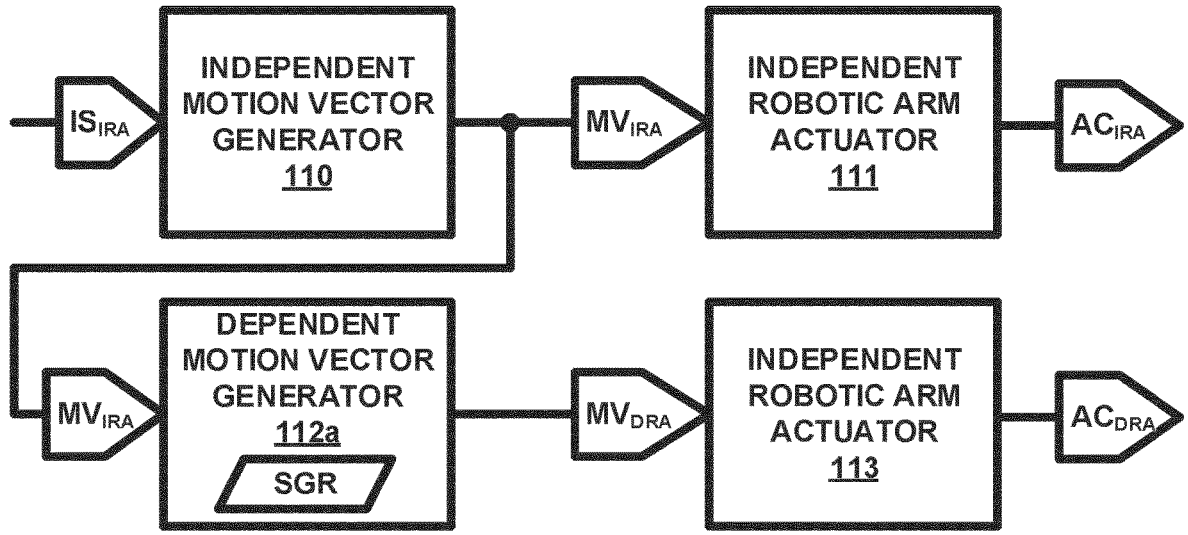
FIGS. 15A and 15B illustrate exemplary embodiments of a motion dependency robot controller for an independent surgical robotic arm and a dependent surgical robotic arm in accordance with the inventive principles of the present disclosure.

Referring to FIG. 15A, an embodiment of motion dependency robot controller 104 employs application modules 110-113 for executing flowchart 30 (FIG. 7).

Specifically, in accordance with stage S32 of flowchart 30, an independent motion vector generator 110 processes input signal $IS_{IRA}$ to generate motion vector $MV_{IRA}$, and an independent surgical robotic arm actuator 111 processes motion vector $MV_{IRA}$ to generate actuation commands $AC_{IRA}$.

Further, in accordance with stage S34 of flowchart 30, a dependent motion vector generator 112a processes motion vector $MV_{IRA}$ in the context of spatial geometric relationship SGR to generate motion vector $MV_{DRA}$, and an independent surgical robotic arm actuator 111 processes motion vector $MV_{DRA}$ to generate actuation commands $AC_{DRA}$.

Figure 15B:
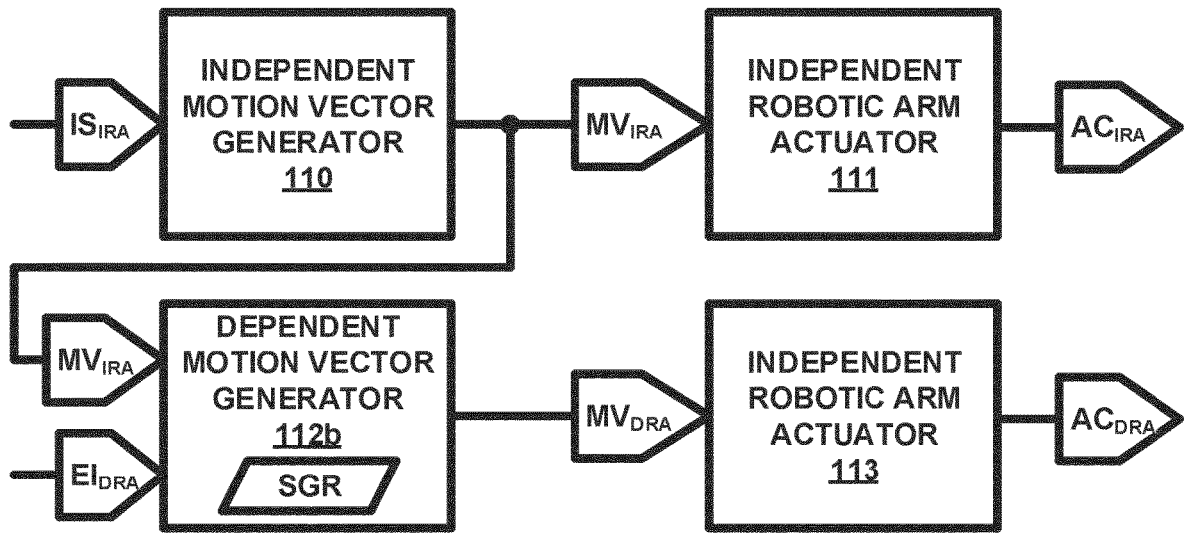

Referring to FIG. 15B, an embodiment of motion dependency robot controller 104 employs application modules 110-113 for executing flowchart 40 (FIG. 9).

Specifically, in accordance with stage S42 of flowchart 40, independent motion vector generator 110 processes input signal $IS_{IRA}$ to generate motion vector $MV_{IRA}$, and an independent surgical robotic arm actuator 111 processes motion vector $MV_{IRA}$ to generate actuation commands $AC_{IRA}$.

Further, in accordance with stage S44 of flowchart 40, a dependent motion vector generator 112b processes motion vector $MV_{IRA}$ and environment signal $EI_{DRA}$ in the context of spatial geometric relationship SGR to generate motion vector $MV_{DRA}$, and independent surgical robotic arm actuator 111 processes motion vector $MV_{DRA}$ to generate actuation commands $AC_{DRA}$.

Figure 16A:
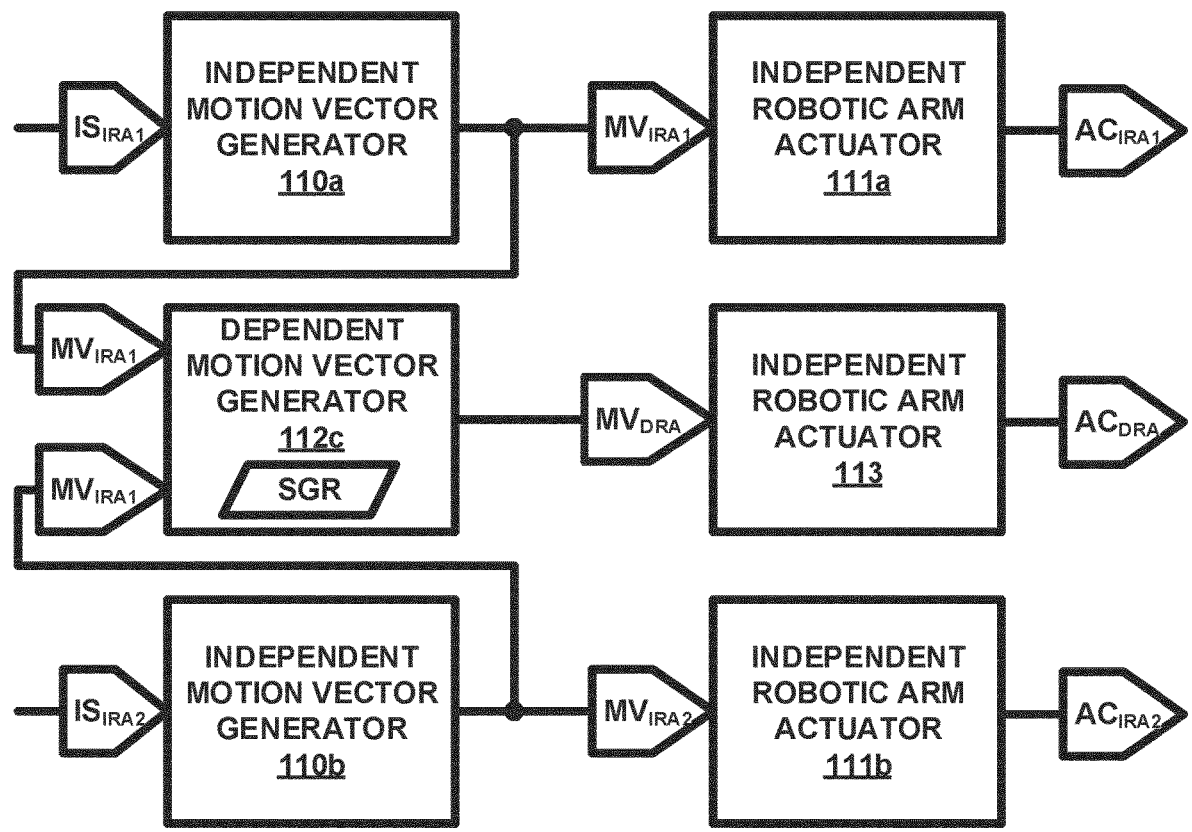
FIGS. 16A and 16B illustrate exemplary embodiments of a motion dependency robot controller for a pair of independent surgical robotic arms and a dependent surgical robotic arm in accordance with the inventive principles of the present disclosure.

Referring to FIG. 16A, an embodiment of motion dependency robot controller 104 employs components 110-113 for executing flowchart 50 (FIG. 12).

Specifically, in accordance with stage S52 of flowchart 50, an independent motion vector generator 110a processes input signal $IS_{IRA1}$ to generate motion vector $MV_{IRA1}$, an independent surgical robotic arm actuator 111a processes motion vector $MV_{IRA1}$ to generate actuation commands $AC_{IRA1}$, an independent motion vector generator 110b processes input signal $IS_{IRA2}$ to generate motion vector $MV_{IRA2}$, and an independent surgical robotic arm actuator 111b processes motion vector $MV_{IRA2}$ to generate actuation commands $AC_{IRA2}$.

Further, in accordance with stage S54 of flowchart 50, a dependent motion vector generator 112c processes motion vector $MV_{IRA1}$ and motion vector $MV_{IRA2}$ in the context of spatial geometric relationship SGR to generate motion vector $MV_{DRA}$, and an independent surgical robotic arm actuator 111 processes motion vector $MV_{DRA}$ to generate actuation commands $AC_{DRA}$.

Figure 16B:
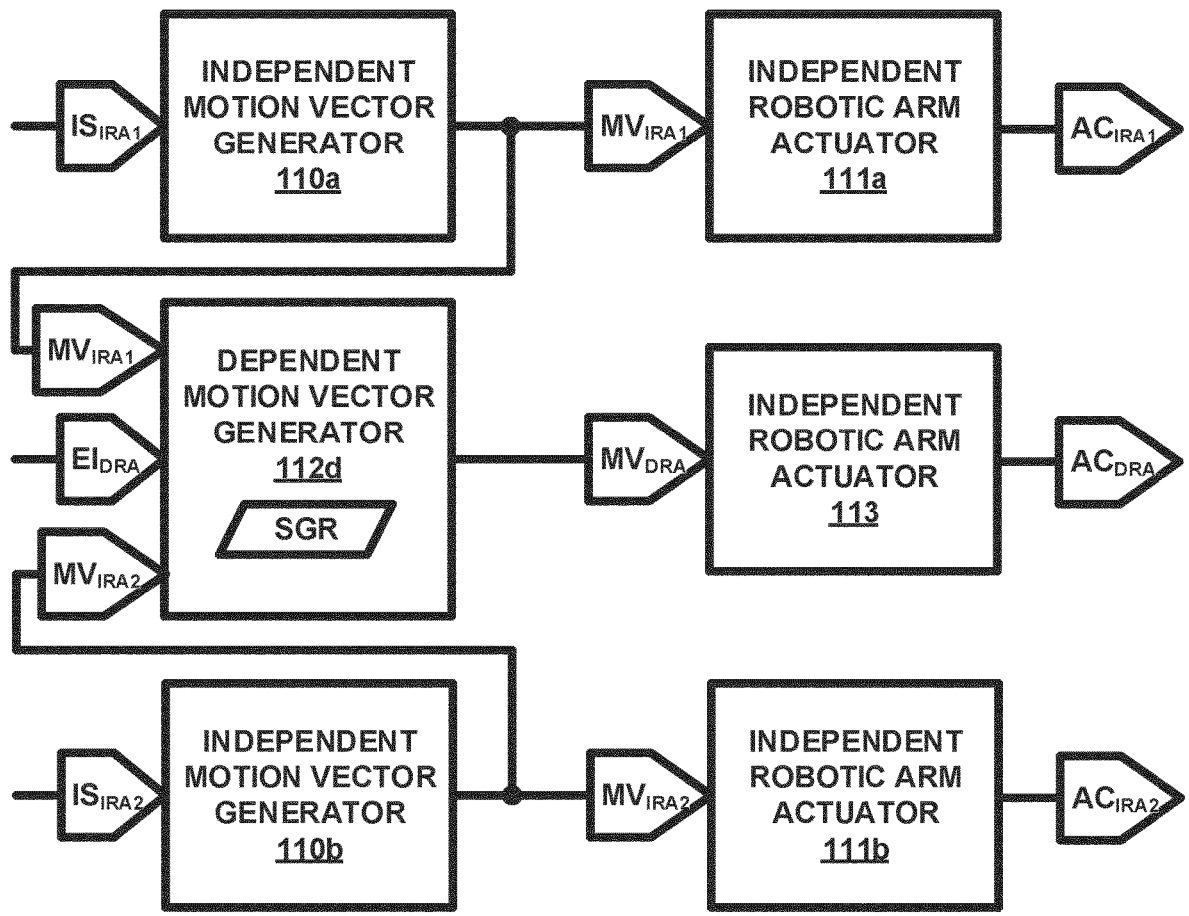

Referring to FIG. 16B, an embodiment of motion dependency robot controller 104 employs components 110-113 for executing flowchart 60 (FIG. 13).

Specifically, in accordance with stage S62 of flowchart 60, an independent motion vector generator 110a processes input signal $IS_{IRA1}$ to generate motion vector $MV_{IRA1}$, an independent surgical robotic arm actuator 111a processes motion vector $MV_{IRA1}$ to generate actuation commands $AC_{IRA1}$, an independent motion vector generator 110b processes input signal $IS_{IRA2}$ to generate motion vector $MV_{IRA2}$, and an independent surgical robotic arm actuator 111b processes motion vector $MV_{IRA2}$ to generate actuation commands $AC_{IRA2}$.

Further, in accordance with stage S64 of flowchart 60, a dependent motion vector generator 112d processes motion vector $MV_{IRA1}$, motion vector $MV_{IRA2}$ and environment signal $EI_{DRA}$ in the context of spatial geometric relationship SGR to generate motion vector $MV_{DRA}$, and an independent surgical robotic arm actuator 111 processes motion vector $MV_{DRA}$ to generate actuation commands $AC_{DRA}$.

Referring to FIGS. 1-16, those having ordinary skill in the art will appreciate numerous benefits of the present disclosure including, but not limited to, an improvement over surgical robot systems by the inventions of the present disclosure in providing an intuitive control of multi-robotic arm surgical tasks with a reduced need to switch control between the robotic arms.

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive motion dependency surgical robotic arm control, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A motion dependency surgical robotic system, comprising:
   an independent robotic arm including a first surgical instrument;
   a dependent robotic arm including a second surgical instrument; and
   a motion dependency robot controller in communication with the independent robotic arm and the dependent robotic arm, the motion dependency robot controller structurally configured to:
      control a motion of the independent robotic arm within a coordinate space responsive to an input signal indicative of the motion of the independent robotic arm within the coordinate space; and
      control a motion of the dependent robotic arm within the coordinate space as a function of a spatial geometric relationship between the independent robotic arm and the dependent robotic arm within the coordinate space,
      wherein the spatial geometric relationship defines a procedural synchronization between the independent robotic arm and the dependent robotic arm in a synchronized execution of a surgical task by the first surgical instrument and the second surgical instrument, the procedural synchronization providing, for one or more steps of the surgical task, an adjustment in relative positioning of the dependent robotic arm and the independent robotic arm.

2. The motion dependency surgical robotic system of claim 1, wherein an orientation of the dependent robotic arm within the coordinate space is dependent upon an orientation of the independent robotic arm within the coordinate space.

3. The motion dependency surgical robotic system of claim 1, wherein an orientation of the dependent robotic arm within the coordinate space is independent of an orientation of the independent robotic arm within the coordinate space.

4. The motion dependency surgical robotic system of claim 1, wherein a linear vector further defines the spatial geometric relationship between the independent robotic arm and the dependent robotic arm within the coordinate space.

5. The motion dependent surgical robotic system of claim 4, wherein one of:
   a magnitude of the linear vector is variable; or
   a direction of the linear vector is one of parallel to an axis of the coordinate space, traversal across a plane of the coordinate space or radial to a center of a sphere within the coordinate space.

6. The motion dependency surgical robotic system of claim 1, wherein an angular vector further defines the spatial geometric relationship between the independent robotic arm and the dependent robotic arm.

7. The motion dependent surgical robotic system of claim 6, wherein one of:
   a magnitude of the angular vector is variable; or
   a direction of the angular vector is traversal across a plane of the coordinate space.

8. The motion dependency surgical robotic system of claim 1, wherein the motion dependency robot controller is structurally configured to compute the procedural synchronization based on at least one of an explicit function and a lookup table.

9. The motion dependency surgical robotic system of claim 1, wherein the motion dependency robot controller is further structurally configured to control the motion of the dependent robotic arm within the coordinate space as a function of an obstacle avoidance by the dependent robotic arm within the coordinate space.

10. The motion dependency surgical robotic system of claim 1, wherein the motion dependent robot controller includes:
    an independent motion vector generator structurally configured to generate an independent motion vector signal for controlling the motion of the independent robotic arm within a coordinate space responsive to an input signal indicative of the motion of the independent robotic arm within the coordinate space;
    an independent robotic arm actuator structurally configured to generate independent actuation commands instructive of the motion of the independent robotic arm within the coordinate space responsive to a generation of the independent motion vector signal by the independent motion vector generator;
    a dependent motion vector generator structurally configured to generate, responsive to the generation of the independent motion vector signal by the independent motion vector generator, a dependent motion vector signal for controlling the motion of the dependent robotic arm within the coordinate space as the function of the spatial geometric relationship between the independent robotic arm and the dependent robotic arm within the coordinate space; and
    a dependent robotic arm actuator structurally configured to generate actuation commands instructive of the motion of the dependent robotic arm within the coordinate space responsive to a generation of the dependent motion vector signal by the dependent motion vector generator.

11. The motion dependency surgical robot system of claim 10,
    wherein the independent motion vector includes at least one of a magnitude and a direction indicative of a positioning of the independent robotic arm within the coordinate space; and
    wherein the dependent motion vector includes at least one of a magnitude and a direction indicative of a positioning of the dependent robotic arm within the coordinate space.

12. The motion dependency surgical robot system of claim 10,
    wherein the independent motion vector includes at least one of a magnitude and a direction indicative of a velocity of the independent robotic arm within the coordinate space; and
    wherein the dependent motion vector includes at least one of a magnitude and a direction indicative of a velocity of the dependent robotic arm within the coordinate space.

13. The motion dependency surgical robotic system of claim 1, wherein:
the procedural synchronization providing, upon completion of a particular step of the surgical task by the independent robotic arm, a subsequent adjustment in position of the dependent robotic arm relative to position of the independent robotic arm for executing a subsequent step of the surgical task; and
based on the subsequent adjustment, the motion dependency robot controller automatically computes an adjusted position for the dependent robotic arm and moves the dependent robotic arm to the adjusted position to execute the subsequent step.

14. A motion dependency robot controller for controlling an independent robotic arm and a dependent robotic arm, the motion dependency robot controller comprising:
an independent motion vector generator structurally configured to generate an independent motion vector signal for controlling a motion of an independent robotic arm within a coordinate space responsive to an input signal indicative of the motion of the independent robotic arm within the coordinate space;
an independent robotic arm actuator structurally configured to generate independent actuation commands instructive of the motion of the independent robotic arm within the coordinate space responsive to a generation of the independent motion vector signal by the independent motion vector generator;
a dependent motion vector generator structurally configured to generate, responsive to the generation of the independent motion vector signal by the independent motion vector generator, a dependent motion vector signal for controlling a motion of the dependent robotic arm within the coordinate space as a function of a spatial geometric relationship between the independent robotic arm and the dependent robotic arm within the coordinate space,
wherein the spatial geometric relationship defines a procedural synchronization between the independent robotic arm and the dependent robotic arm in a synchronized execution of a surgical task by a first surgical instrument of the independent robotic arm and a second surgical instrument of the dependent robotic arm, the procedural synchronization providing, for one or more steps of the surgical task, an adjustment in relative positioning of the dependent robotic arm and the independent robotic arm; and
a dependent robotic arm actuator structurally configured to generate actuation commands instructive of the motion of the dependent robotic arm within the coordinate space responsive to a generation of the dependent motion vector signal by the dependent motion vector generator.

15. The motion dependency robot controller of claim 14, wherein the independent motion vector includes at least one of a magnitude and a direction indicative of at least one of a positioning and a velocity of the independent robotic arm within the coordinate space; and
wherein the dependent motion vector includes at least one of a magnitude and a direction indicative of at least one of a positioning and a velocity of the dependent robotic arm within the coordinate space.

16. The motion dependency robot controller of claim 14, wherein the motion dependency robot controller is structurally configured to compute the procedural synchronization based on at least one of an explicit function and a lookup table.

17. A motion dependency robot control method comprising:
providing a motion dependency surgical robotic system including an independent robotic arm, a dependent robotic arm , and a motion dependency robot controller;
controlling, by a motion dependency robot controller, a motion of the independent robotic arm within a coordinate space responsive to an input signal indicative of the motion of the independent robotic arm within the coordinate space; and
controlling, by the motion dependency robot controller, a motion of the dependent robotic arm within the coordinate space as a function of a spatial geometric relationship between the independent robotic arm and the dependent robotic arm within the coordinate space,
wherein the spatial geometric relationship defines a procedural synchronization between the independent robotic arm and the dependent robotic arm in a synchronized execution of a surgical task by the first surgical instrument and the second surgical instrument, the procedural synchronization providing, for one or more steps of the surgical task, an adjustment in relative positioning of the dependent robotic arm and the independent robotic arm.

18. The motion dependency robot control method of claim 17, wherein a linear vector defines the spatial geometric relationship between the independent robotic arm and the dependent robotic arm within the coordinate space.

19. The motion dependency robot control method of claim 17, wherein an angular vector defines the spatial geometric relationship between the independent robotic arm and the dependent robotic arm within the coordinate space.

20. The motion dependency robot control method of claim 17, wherein a procedural synchronization defines the spatial geometric relationship between the independent robotic arm and the dependent robotic arm.

21. The motion dependency robot control method of claim 17, further comprising controlling, by the motion dependency robot controller, the motion of the dependent robotic arm within the coordinate space as a function of an obstacle avoidance by the dependent robotic arm within the coordinate space.

* * * * *